United States Patent
Rashbaum et al.

(10) Patent No.: US 8,979,932 B2
(45) Date of Patent: Mar. 17, 2015

(54) INTERVERTEBRAL DISC PROSTHESIS

(75) Inventors: Ralph Rashbaum, Plano, TX (US); Kee D Kim, Davis, CA (US); Hyun Bae, Santa Monica, CA (US)

(73) Assignee: LDR Medical, Rosières Près Troyes (FR)

( * ) Notice: Subject to any disclaimer, the term of this patent is extended or adjusted under 35 U.S.C. 154(b) by 0 days.

(21) Appl. No.: 12/955,898

(22) Filed: Nov. 29, 2010

(65) Prior Publication Data

US 2011/0077739 A1 Mar. 31, 2011

Related U.S. Application Data

(63) Continuation of application No. 11/341,007, filed on Jan. 27, 2006, now Pat. No. 7,842,088.

(30) Foreign Application Priority Data

Sep. 23, 2005 (FR) ...................................... 05 09740

(51) Int. Cl.
*A61F 2/44* (2006.01)
*A61F 2/30* (2006.01)
*A61B 17/064* (2006.01)

(52) U.S. Cl.
CPC ..... *A61F 2/4425* (2013.01); *A61F 2002/30576* (2013.01); *A61F 2002/30365* (2013.01);
(Continued)

(58) Field of Classification Search
CPC .......................... A61F 2/4425; A61F 2002/443
USPC ............................................ 623/17.11–17.16
See application file for complete search history.

(56) References Cited

U.S. PATENT DOCUMENTS 3,374,786 A 3/1968 Callender et al.
3,791,380 A 2/1974 Dawidowski
(Continued)

FOREIGN PATENT DOCUMENTS

CA 2472708 2/2005
CA 2533473 3/2011
(Continued)

OTHER PUBLICATIONS

LDR Medical, by its attorneys; Amendment after Final in U.S. Appl. No. 10/476,565; Nov. 29, 2007; USPTO; Alexandria, Virgina; All Pages.
(Continued)

*Primary Examiner* — Ellen C Hammond
(74) *Attorney, Agent, or Firm* — Denko Coburn Lauff LLP

(57) ABSTRACT

The invention relates to an intervertebral disc prosthesis comprising at least two plates, namely first and second plates, articulated about each other by means of a curved surface, namely articulation, of at least one of the plates, each of the plates comprising a surface known as a contact surface, intended to be in contact with a vertebral plate of one of the vertebrae between which the prosthesis is intended to be inserted, this contact surface for each of the plates comprising a geometrical centre at equal distance from at least two diametrically opposite points located on the periphery of the plate, in which the geometric centres of the plates are not vertically aligned, this off-setting of the geometrical centres of the plates engendering an off-setting of the edges of the plates in at least one direction perpendicular to the vertical axis of the spinal column.

24 Claims, 4 Drawing Sheets

(52) U.S. Cl.
CPC . *A61F2002/30884* (2013.01); *A61F 2002/305* (2013.01); *A61F 2002/30878* (2013.01); *A61F 2220/0025* (2013.01); *A61B 2017/0647* (2013.01); *A61F 2002/30369* (2013.01); *A61F 2002/30616* (2013.01); *A61F 2002/30904* (2013.01); *A61B 17/0642* (2013.01); *A61F 2002/443* (2013.01); *A61F 2002/30662* (2013.01); *A61F 2002/30331* (2013.01); *A61F 2220/0033* (2013.01); *A61F 2/30734* (2013.01)
USPC ........................................................ 623/17.14

(56) References Cited

U.S. PATENT DOCUMENTS

| | | | |
|---|---|---|---|
| 3,892,232 A | 7/1975 | Neufeld | |
| 4,009,712 A | 3/1977 | Burstein et al. | |
| 4,135,506 A | 1/1979 | Ulrich | |
| 4,175,555 A | 11/1979 | Herbert | |
| 4,185,762 A | 1/1980 | Froehlich | |
| 4,237,875 A | 12/1980 | Termanini | |
| 4,379,451 A | 4/1983 | Getscher | |
| 4,409,974 A | 10/1983 | Freedland | |
| 4,432,358 A | 2/1984 | Fixel | |
| 4,488,543 A | 12/1984 | Tornier | |
| 4,494,535 A | 1/1985 | Haig | |
| 4,519,100 A | 5/1985 | Wills et al. | |
| 4,561,432 A | 12/1985 | Mazor | |
| 4,612,920 A | 9/1986 | Lower | |
| 4,621,629 A | 11/1986 | Koeneman | |
| 4,632,101 A | 12/1986 | Freedland | |
| 4,653,489 A | 3/1987 | Tronzo | |
| 4,657,001 A | 4/1987 | Fixel | |
| 4,664,305 A | 5/1987 | Blake, III et al. | |
| 4,721,103 A | 1/1988 | Freedland | |
| 4,759,352 A | 7/1988 | Lozier | |
| 4,787,378 A | 11/1988 | Sodhi | |
| 4,790,303 A | 12/1988 | Steffee | |
| 4,791,918 A | 12/1988 | Von Hasselbach | |
| 4,898,156 A | 2/1990 | Gatturna et al. | |
| 4,946,468 A | 8/1990 | Li | |
| 4,964,403 A | 10/1990 | Karas et al. | |
| 4,968,315 A | 11/1990 | Gatturna | |
| 4,969,887 A | 11/1990 | Sodhi | |
| 4,973,332 A | 11/1990 | Kummer | |
| 4,973,333 A | 11/1990 | Treharne | |
| 5,002,550 A | 3/1991 | Li | |
| 5,007,910 A | 4/1991 | Anapliotis et al. | |
| 5,032,125 A | 7/1991 | Durham et al. | |
| 5,041,114 A | 8/1991 | Chapman et al. | |
| 5,041,116 A | 8/1991 | Wilson | |
| 5,046,513 A | 9/1991 | Gatturna et al. | |
| 5,057,103 A | 10/1991 | Davis | |
| 5,062,851 A | 11/1991 | Branemark | |
| 5,087,266 A | 2/1992 | Connell et al. | |
| 5,098,433 A | 3/1992 | Freedland | |
| 5,116,336 A | 5/1992 | Frigg | |
| 5,129,901 A | 7/1992 | Decoste | |
| 5,176,681 A | 1/1993 | Lawes et al. | |
| 5,192,303 A | 3/1993 | Gatturna et al. | |
| 5,207,679 A | 5/1993 | Li | |
| 5,217,486 A | 6/1993 | Rice et al. | |
| 5,234,447 A | 8/1993 | Kaster et al. | |
| 5,242,448 A | 9/1993 | Pettine et al. | |
| 5,258,009 A | 11/1993 | Conners | |
| 5,300,074 A | 4/1994 | Frigg | |
| 5,324,292 A | 6/1994 | Meyers | |
| 5,342,394 A | 8/1994 | Matsuno et al. | |
| 5,356,410 A | 10/1994 | Pennig | |
| 5,356,413 A | 10/1994 | Martins et al. | |
| 5,372,599 A | 12/1994 | Martins | |
| 5,417,692 A | 5/1995 | Goble et al. | |
| 5,417,712 A | 5/1995 | Whittaker et al. | |
| 5,429,641 A | 7/1995 | Gotfried | |
| 5,437,674 A | 8/1995 | Worcel et al. | |
| 5,443,514 A | 8/1995 | Steffee | |
| 5,456,721 A | 10/1995 | Legrand | |
| 5,458,601 A | 10/1995 | Young, Jr. et al. | |
| 5,472,452 A | 12/1995 | Trott | |
| 5,478,342 A | 12/1995 | Kohrs | |
| 5,489,210 A | 2/1996 | Hanosh | |
| 5,507,754 A | 4/1996 | Green et al. | |
| 5,522,845 A | 6/1996 | Wenstrom, Jr. | |
| 5,522,899 A | 6/1996 | Michelson | |
| 5,531,792 A | 7/1996 | Huene | |
| 5,534,004 A | 7/1996 | Santangelo | |
| 5,549,617 A | 8/1996 | Green et al. | |
| 5,554,191 A | 9/1996 | Lahille et al. | |
| 5,562,689 A | 10/1996 | Green et al. | |
| 5,571,104 A | 11/1996 | Li | |
| 5,571,189 A | 11/1996 | Kuslich | |
| 5,578,035 A | 11/1996 | Lin | |
| 5,591,168 A | 1/1997 | Judet et al. | |
| 5,593,409 A | 1/1997 | Michelson | |
| 5,609,635 A | 3/1997 | Michelson | |
| 5,613,974 A | 3/1997 | Andreas et al. | |
| 5,620,012 A | 4/1997 | Benderev et al. | |
| 5,643,321 A | 7/1997 | McDevitt | |
| 5,655,698 A | 8/1997 | Yoon et al. | |
| 5,683,464 A | 11/1997 | Wagner et al. | |
| 5,702,449 A | 12/1997 | McKay | |
| 5,766,253 A | 6/1998 | Brosnahan, III | |
| 5,800,547 A | 9/1998 | Schafer, et al. | |
| 5,800,550 A | 9/1998 | Sertich | |
| 5,807,403 A | 9/1998 | Beyar et al. | |
| 5,895,427 A | 4/1999 | Kuslich et al. | |
| 5,968,098 A | 10/1999 | Winslow | |
| 5,980,522 A | 11/1999 | Koros et al. | |
| 6,066,175 A | 5/2000 | Henderson, et al. | |
| 6,096,080 A | 8/2000 | Nicholson et al. | |
| 6,099,531 A | 8/2000 | Bonutti | |
| 6,102,950 A | 8/2000 | Vaccaro | |
| 6,129,763 A | 10/2000 | Chauvin et al. | |
| 6,214,050 B1 | 4/2001 | Huene | |
| 6,241,769 B1 | 6/2001 | Nicholson et al. | |
| 6,258,094 B1 | 7/2001 | Nicholson et al. | |
| 6,261,293 B1 | 7/2001 | Nicholson et al. | |
| 6,287,308 B1 | 9/2001 | Betz et al. | |
| 6,302,914 B1 | 10/2001 | Michelson | |
| 6,342,074 B1 | 1/2002 | Simpson | |
| 6,371,987 B1 | 4/2002 | Weiland, et al. | |
| 6,419,703 B1 | 7/2002 | Fallin et al. | |
| 6,423,063 B1 | 7/2002 | Bonutti | |
| 6,447,544 B1 | 9/2002 | Michelson | |
| 6,447,546 B1 * | 9/2002 | Bramlet et al. | 623/17.16 |
| 6,485,517 B1 | 11/2002 | Michelson | |
| 6,500,205 B1 | 12/2002 | Michelson | |
| 6,540,753 B2 | 4/2003 | Cohen | |
| 6,558,423 B1 | 5/2003 | Michelson | |
| 6,558,424 B2 * | 5/2003 | Thalgott | 623/17.16 |
| 6,565,605 B2 | 5/2003 | Goble et al. | |
| 6,607,530 B1 | 8/2003 | Carl et al. | |
| 6,648,893 B2 | 11/2003 | Dudasik | |
| 6,679,887 B2 | 1/2004 | Nicholson et al. | |
| 6,709,458 B2 | 3/2004 | Michelson | |
| 6,716,247 B2 | 4/2004 | Michelson | |
| 6,723,128 B2 | 4/2004 | Uk | |
| 6,749,636 B2 | 6/2004 | Michelson | |
| 6,770,096 B2 | 8/2004 | Bolger et al. | |
| 6,793,679 B2 | 9/2004 | Michelson | |
| 6,800,093 B2 | 10/2004 | Nicholson et al. | |
| 6,805,714 B2 | 10/2004 | Sutcliffe | |
| 6,808,537 B2 | 10/2004 | Michelson | |
| 6,835,206 B2 | 12/2004 | Jackson | |
| 6,849,093 B2 | 2/2005 | Michelson | |
| 6,890,355 B2 | 5/2005 | Michelson | |
| 6,902,580 B2 | 6/2005 | Fallin et al. | |
| 6,916,340 B2 | 7/2005 | Metzger et al. | |
| 6,923,811 B1 | 8/2005 | Carl et al. | |
| 6,923,830 B2 | 8/2005 | Michelson | |
| 6,936,071 B1 | 8/2005 | Marnay et al. | |
| 6,955,691 B2 | 10/2005 | Chae et al. | |
| 6,962,606 B2 | 11/2005 | Michelson | |
| 6,972,019 B2 | 12/2005 | Michelson | |

(56) References Cited

U.S. PATENT DOCUMENTS

| | | |
|---|---|---|
| 6,972,035 B2 | 12/2005 | Michelson |
| 6,981,975 B2 | 1/2006 | Michelson |
| 6,984,234 B2 | 1/2006 | Bray |
| 7,001,385 B2 | 2/2006 | Bonutti |
| 7,008,453 B1 | 3/2006 | Michelson |
| 7,033,394 B2 | 4/2006 | Michelson |
| 7,041,135 B2 | 5/2006 | Michelson |
| 7,041,136 B2 | 5/2006 | Goble et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,112,206 B2 | 9/2006 | Michelson |
| 7,118,579 B2 | 10/2006 | Michelson |
| 7,118,598 B2 | 10/2006 | Michelson |
| 7,128,760 B2 | 10/2006 | Michelson |
| 7,128,761 B2 | 10/2006 | Kuras et al. |
| 7,147,665 B1 | 12/2006 | Bryan et al. |
| 7,163,561 B2 | 1/2007 | Michelson |
| 7,179,294 B2 | 2/2007 | Eisermann et al. |
| 7,211,112 B2 | 5/2007 | Baynham et al. |
| 7,217,291 B2 | 5/2007 | Zucherman et al. |
| 7,217,292 B2 | 5/2007 | Ralph et al. |
| 7,217,293 B2 | 5/2007 | Branch, Jr. |
| 7,223,289 B2 | 5/2007 | Trieu et al. |
| 7,232,463 B2 | 6/2007 | Falahee |
| 7,232,464 B2 | 6/2007 | Mathieu et al. |
| 7,326,248 B2 | 2/2008 | Michelson |
| 7,326,250 B2 | 2/2008 | Beaurain et al. |
| 7,410,501 B2 | 8/2008 | Michelson |
| 7,419,505 B2 | 9/2008 | Fleischmann et al. |
| 7,431,735 B2 | 10/2008 | Liu et al. |
| 7,435,262 B2 | 10/2008 | Michelson |
| 7,442,209 B2 | 10/2008 | Michelson |
| 7,445,635 B2 | 11/2008 | Fallin et al. |
| 7,445,636 B2 | 11/2008 | Michelson |
| 7,455,692 B2 | 11/2008 | Michelson |
| 7,465,317 B2 | 12/2008 | Malberg et al. |
| 7,481,840 B2 | 1/2009 | Zucherman et al. |
| 7,494,507 B2 | 2/2009 | Dixon et al. |
| 7,494,508 B2 | 2/2009 | Zeegers |
| 7,503,933 B2 | 3/2009 | Michelson |
| 7,517,363 B2 | 4/2009 | Rogers et al. |
| 7,540,882 B2 | 6/2009 | Michelson |
| 7,566,345 B1 | 7/2009 | Fallin et al. |
| 7,575,599 B2 | 8/2009 | de Villiers et al. |
| 7,575,600 B2 | 8/2009 | Zucherman et al. |
| 7,588,590 B2 | 9/2009 | Chervitz et al. |
| 7,591,851 B2 | 9/2009 | Winslow et al. |
| 7,594,931 B2 | 9/2009 | Louis et al. |
| 7,594,932 B2 | 9/2009 | Aferzon et al. |
| 7,601,170 B2 | 10/2009 | Winslow et al. |
| 7,608,107 B2 | 10/2009 | Michelson |
| 7,611,538 B2 | 11/2009 | Belliard et al. |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,956 B2 | 11/2009 | Paul et al. |
| 7,621,958 B2 | 11/2009 | Zdeblick et al. |
| 7,632,282 B2 | 12/2009 | Dinville |
| 7,637,951 B2 | 12/2009 | Michelson |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |
| 7,682,396 B2 | 3/2010 | Beaurain et al. |
| 7,695,516 B2 * | 4/2010 | Zeegers ............... 623/17.14 |
| 7,695,517 B2 | 4/2010 | Benzel et al. |
| 7,708,776 B1 | 5/2010 | Blain et al. |
| 7,717,959 B2 | 5/2010 | William et al. |
| 7,727,280 B2 | 6/2010 | McLuen |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,771,478 B2 * | 8/2010 | Navarro et al. ............ 623/17.15 |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |
| 7,842,088 B2 | 11/2010 | Rashbaum et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,896,919 B2 | 3/2011 | Belliard et al. |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 7,998,211 B2 * | 8/2011 | Baccelli et al. ............ 623/17.15 |
| 8,002,835 B2 | 8/2011 | Zeegers |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,114,082 B2 | 2/2012 | Boyajian et al. |
| 8,257,439 B2 | 9/2012 | Zeegers |
| 8,267,999 B2 | 9/2012 | Beaurain et al. |
| 8,343,219 B2 | 1/2013 | Allain et al. |
| 8,388,684 B2 | 3/2013 | Bao et al. |
| 8,439,931 B2 | 5/2013 | Dinville |
| 2002/0035400 A1 | 3/2002 | Bryan et al. |
| 2002/0040243 A1 | 4/2002 | Attali et al. |
| 2002/0070565 A1 * | 6/2002 | Szapucki et al. ............... 292/228 |
| 2002/0161444 A1 | 10/2002 | Choi |
| 2002/0165613 A1 * | 11/2002 | Lin et al. .................... 623/17.11 |
| 2002/0193880 A1 | 12/2002 | Fraser |
| 2003/0069586 A1 | 4/2003 | Errico et al. |
| 2003/0074075 A1 | 4/2003 | Thomas, Jr. et al. |
| 2003/0093153 A1 | 5/2003 | Banick et al. |
| 2003/0093156 A1 | 5/2003 | Metzger et al. |
| 2003/0135279 A1 | 7/2003 | Michelson |
| 2003/0187436 A1 | 10/2003 | Bolger et al. |
| 2003/0195514 A1 | 10/2003 | Trieu et al. |

(56) References Cited

U.S. PATENT DOCUMENTS

| | | |
|---|---|---|
| 2004/0010312 A1 | 1/2004 | Enayati |
| 2004/0024406 A1 | 2/2004 | Ralph et al. |
| 2004/0083000 A1 | 4/2004 | Keller et al. |
| 2004/0153157 A1 | 8/2004 | Keller |
| 2004/0158254 A1 | 8/2004 | Eisermann |
| 2004/0158328 A1 | 8/2004 | Eisermann |
| 2004/0210219 A1 | 10/2004 | Bray |
| 2004/0210313 A1 | 10/2004 | Michelson |
| 2004/0254643 A1 | 12/2004 | Jackson |
| 2005/0015095 A1 | 1/2005 | Keller |
| 2005/0015149 A1 | 1/2005 | Michelson |
| 2005/0033428 A1 | 2/2005 | Keller |
| 2005/0033435 A1 | 2/2005 | Belliard et al. |
| 2005/0038512 A1 | 2/2005 | Michelson |
| 2005/0038516 A1 | 2/2005 | Spoonamore |
| 2005/0049590 A1 | 3/2005 | Alleyne et al. |
| 2005/0060037 A1 | 3/2005 | Michelson |
| 2005/0065608 A1 | 3/2005 | Michelson |
| 2005/0065611 A1 * | 3/2005 | Huppert et al. ............ 623/17.15 |
| 2005/0131544 A1 | 6/2005 | Kuras et al. |
| 2005/0143733 A1 | 6/2005 | Petit |
| 2005/0143825 A1 | 6/2005 | Enayati |
| 2005/0154462 A1 | 7/2005 | Zucherman et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2006/0016768 A1 | 1/2006 | Grichar et al. |
| 2006/0036261 A1 | 2/2006 | McDonnell |
| 2006/0036325 A1 | 2/2006 | Paul et al. |
| 2006/0058878 A1 | 3/2006 | Michelson |
| 2006/0085076 A1 | 4/2006 | Krishna et al. |
| 2006/0085077 A1 | 4/2006 | Cook et al. |
| 2006/0089717 A1 | 4/2006 | Krishna et al. |
| 2006/0095136 A1 | 5/2006 | McLuen |
| 2006/0129244 A1 | 6/2006 | Ensign |
| 2006/0136063 A1 * | 6/2006 | Zeegers ...................... 623/17.14 |
| 2006/0142863 A1 * | 6/2006 | Fraser et al. ................ 623/17.13 |
| 2006/0178745 A1 | 8/2006 | Bartish et al. |
| 2006/0206208 A1 | 9/2006 | Michelson |
| 2006/0241764 A1 | 10/2006 | Michelson |
| 2006/0253201 A1 | 11/2006 | McLuen |
| 2006/0259147 A1 | 11/2006 | Krishna et al. |
| 2007/0010886 A1 | 1/2007 | Banick et al. |
| 2007/0016297 A1 | 1/2007 | Johnson |
| 2007/0032871 A1 | 2/2007 | Michelson |
| 2007/0118223 A1 | 5/2007 | Allard et al. |
| 2007/0123985 A1 | 5/2007 | Errico et al. |
| 2007/0162137 A1 | 7/2007 | Kloss et al. |
| 2007/0179623 A1 | 8/2007 | Trieu et al. |
| 2007/0250167 A1 | 10/2007 | Bray et al. |
| 2007/0250168 A1 | 10/2007 | Lechmann et al. |
| 2007/0260249 A1 | 11/2007 | Boyajian et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2007/0288094 A1 | 12/2007 | Krishna et al. |
| 2007/0299524 A1 | 12/2007 | Rivin |
| 2008/0027547 A1 | 1/2008 | Yu et al. |
| 2008/0027550 A1 | 1/2008 | Link et al. |
| 2008/0033555 A1 | 2/2008 | Link et al. |
| 2008/0033562 A1 | 2/2008 | Krishna et al. |
| 2008/0161930 A1 | 7/2008 | Carls et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1 | 10/2008 | Ralph et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0076615 A1 | 3/2009 | Duggal et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2010/0004664 A1 | 1/2010 | Boyajian et al. |
| 2010/0049259 A1 | 2/2010 | Lambrecht et al. |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |

(56) References Cited

U.S. PATENT DOCUMENTS

| | | | |
|---|---|---|---|
| 2011/0166655 | A1 | 7/2011 | Michelson |
| 2011/0166656 | A1 | 7/2011 | Thalgott et al. |
| 2011/0166657 | A1 | 7/2011 | Thalgott et al. |
| 2011/0166658 | A1 | 7/2011 | Garber et al. |
| 2011/0172774 | A1 | 7/2011 | Varela |
| 2011/0196492 | A1 | 8/2011 | Lambrecht et al. |
| 2011/0196493 | A1 | 8/2011 | Pimenta |
| 2011/0196494 | A1 | 8/2011 | Yedlicka et al. |
| 2011/0202136 | A1 | 8/2011 | Brittan et al. |
| 2011/0208311 | A1 | 8/2011 | Janowski |
| 2011/0208313 | A1 | 8/2011 | Michelson |
| 2011/0230969 | A1 | 9/2011 | Biedermann et al. |
| 2011/0230971 | A1 | 9/2011 | Donner et al. |
| 2011/0264227 | A1 | 10/2011 | Boyajian et al. |
| 2011/0295371 | A1 | 12/2011 | Moskowitz et al. |
| 2011/0301713 | A1 | 12/2011 | Theofilos |
| 2011/0301714 | A1 | 12/2011 | Theofilos |
| 2011/0313528 | A1 | 12/2011 | Laubert et al. |
| 2012/0053693 | A1 | 3/2012 | Zeegers |
| 2013/0226300 | A1 | 8/2013 | Chataigner et al. |

FOREIGN PATENT DOCUMENTS

| | | | |
|---|---|---|---|
| DE | 4328690 | | 3/1995 |
| DE | 29911422 | | 8/1999 |
| DE | 20320454 | | 10/2004 |
| DE | 10323363 | | 12/2004 |
| EP | 0637439 | | 2/1995 |
| EP | 0697200 | | 2/1996 |
| EP | 0951879 | | 10/1999 |
| EP | 1222903 | | 7/2002 |
| EP | 1250898 | | 10/2002 |
| EP | 1287795 | | 3/2003 |
| EP | 1504733 | | 2/2005 |
| FR | 2879436 | | 6/2006 |
| FR | 2880795 | | 7/2006 |
| FR | 2887762 | | 1/2007 |
| FR | 2891135 | | 3/2007 |
| FR | 2893838 | | 6/2007 |
| FR | 2916956 | | 12/2008 |
| WO | WO9011740 | | 10/1990 |
| WO | WO9515133 | | 6/1995 |
| WO | WO9817209 | | 4/1998 |
| WO | WO9956676 | | 11/1999 |
| WO | WO0143620 | | 6/2001 |
| WO | WO02013732 | | 2/2002 |
| WO | WO02058599 | | 8/2002 |
| WO | WO03005939 | | 1/2003 |
| WO | WO03026522 | | 4/2003 |
| WO | WO 03039400 | A2 * | 5/2003 |
| WO | WO03/099172 | | 12/2003 |
| WO | WO2004034935 | | 4/2004 |
| WO | WO2004039291 | | 5/2004 |
| WO | WO 2004041129 | A1 * | 5/2004 |
| WO | WO2004071360 | | 8/2004 |
| WO | WO2004089256 | | 10/2004 |
| WO | WO2005/007044 | | 1/2005 |
| WO | WO2005007040 | | 1/2005 |
| WO | WO2005051243 | | 6/2005 |
| WO | WO2005/063150 | | 7/2005 |
| WO | WO2006016384 | | 2/2006 |
| WO | WO2006047587 | | 5/2006 |
| WO | WO2006062960 | | 6/2006 |
| WO | WO2006120505 | | 11/2006 |
| WO | WO2006130460 | | 12/2006 |
| WO | WO2007000654 | | 1/2007 |
| WO | WO2007034310 | | 3/2007 |
| WO | WO2007063398 | | 6/2007 |
| WO | WO2007078978 | | 7/2007 |
| WO | WO2008099277 | | 8/2008 |
| WO | WO2008149223 | | 12/2008 |
| WO | WO2009033100 | | 3/2009 |
| WO | WO2011080535 | | 7/2011 |
| WO | WO2013/124453 | | 8/2013 |

OTHER PUBLICATIONS

LDR Medical, by its attorneys; Reply to Office Action in U.S. Appl. No. 10/476,565; Jan. 18, 2007; USPTO; Alexandria, Virgina; All Pages.

LDR Medical, by its attorneys; Reply to Office Action in U.S. Appl. No. 10/476,565; Nov. 6, 2007; USPTO; Alexandria, Virgina; All Pages.

U.S. Patent & Trademark Office; Notice of Allowance in U.S. Appl. No. 10/476,565; Nov. 29, 2007; USPTO; Alexandria, Virgina; All Pages.

U.S. Patent & Trademark Office; Office Action in U.S. Appl. No. 10/476,565; Jul. 18, 2006; USPTO; Alexandria, Virgina; All Pages.

U.S. Patent & Trademark Office; Office Action in U.S. Appl. No. 10/476,565; May 7, 2007; USPTO; Alexandria, Virgina; All Pages.

LDR Medical, by its attorneys; Reply to Office Action in U.S. Appl. No. 12/025,677; Apr. 9, 2012; USPTO; Alexandria, Virgina; All Pages.

U.S. Patent & Trademark Office; Office Action in U.S. Appl. No. 12/025,677; Oct. 7, 2011; USPTO; Alexandria, Virgina; All Pages.

U.S. Patent & Trademark Office; Notice of Allowance in U.S. Appl. No. 10/494,418; Sep. 20, 2005; USPTO; Alexandria, Virgina; All Pages.

U.S. Patent & Trademark Office; Notice of Allowance in U.S. Appl. No. 10/533,846; Nov. 4, 2009; USPTO; Alexandria, Virgina; All Pages.

LDR Medical, by its attorneys; Interview Summary and Terminal Disclaimer in U.S. Appl. No. 12/424,364; May 22, 2012; USPTO; Alexandria, Virgina; All Pages.

LDR Medical, by its attorneys; Reply to Office Action in U.S. Appl. No. 12/424,364; Feb. 27, 2012; USPTO; Alexandria, Virgina; All Pages.

LDR Medical, by its attorneys; Reply to Office Action in U.S. Appl. No. 12/424,364; Nov. 18, 2011; USPTO; Alexandria, Virgina; All Pages.

U.S. Patent & Trademark Office; Office Action in U.S. Appl. No. 12/424,364; Jan. 26, 2012; USPTO; Alexandria, Virgina; All Pages.

U.S. Patent & Trademark Office; Office Action in U.S. Appl. No. 12/424,364; May 18, 2011; USPTO; Alexandria, Virgina; All Pages.

U.S. Patent & Trademark Office; Office Action in U.S. Appl. No. 12/424,364; May 23, 2012; USPTO; Alexandria, Virgina; All Pages.

LDR Medical, by its attorneys; Reply to Office Action in U.S. Appl. No. 11/051,710; Apr. 26, 2010; USPTO; Alexandria, Virgina; All Pages.

LDR Medical, by its attorneys; Reply to Office Action in U.S. Appl. No. 11/051,710; Jan. 20, 2011; USPTO; Alexandria, Virgina; All Pages.

LDR Medical, by its attorneys; Reply to Office Action in U.S. Appl. No. 11/051,710; Oct. 11, 2011; USPTO; Alexandria, Virgina; All Pages.

U.S. Patent & Trademark Office; Office Action in U.S. Appl. No. 11/051,710; Apr. 11, 2011; USPTO; Alexandria, Virgina; All Pages.

U.S. Patent & Trademark Office; Office Action in U.S. Appl. No. 11/051,710; Dec. 15, 2011; USPTO; Alexandria, Virgina; All Pages.

U.S. Patent & Trademark Office; Office Action in U.S. Appl. No. 11/051,710; Jul. 20, 2010; USPTO; Alexandria, Virgina; All Pages.

U.S. Patent & Trademark Office; Office Action in U.S. Appl. No. 11/051,710; Oct. 26, 2009; USPTO; Alexandria, Virgina; All Pages.

World Intellectual Property Organization; International Preliminary Report on Patentability for PCT Pub'n. No. WO2005074839; Jan. 16, 2006; WIPO; Geneva, Switzerland; all pages.

World Intellectual Property Organization; Written Opinon of the International Searching Authority for PCT Pub'n. No. WO2005074839; Jun. 24, 2005; WIPO; Geneva, Switzerland; all pages.

LDR Medical, by its attorneys; Reply to Office Action in U.S. Appl. No. 11/098,266; Aug. 22, 2006; USPTO; Alexandria, Virgina; All Pages.

LDR Medical, by its attorneys; Reply to Office Action in U.S. Appl. No. 11/098,266; Feb. 6, 2008; USPTO; Alexandria, Virgina; All Pages.

(56) References Cited

OTHER PUBLICATIONS

LDR Medical, by its attorneys; Reply to Office Action in U.S. Appl. No. 11/098,266; May 23, 2007; USPTO; Alexandria, Virgina; All Pages.
U.S. Patent & Trademark Office; Notice of Allowance in U.S. Appl. No. 11/098,266; Apr. 21, 2008; USPTO; Alexandria, Virgina; All Pages.
U.S. Patent & Trademark Office; Office Action in U.S. Appl. No. 11/098,266; Aug. 6, 2007; USPTO; Alexandria, Virgina; All Pages.
U.S. Patent & Trademark Office; Office Action in U.S. Appl. No. 11/098,266; Mar. 22, 2006; USPTO; Alexandria, Virgina; All Pages.
U.S. Patent & Trademark Office; Office Action in U.S. Appl. No. 11/098,266; Nov. 29, 2006; USPTO; Alexandria, Virginia; All Pages.
World Intellectual Property Organization; International Preliminary Report on Patentability for PCT Pub'n. No. WO2005104996; Jun. 28, 2006; WIPO; Geneva, Switzerland; all pages.
World Intellectual Property Organization; Written Opinon of the International Searching Authority for PCT Pub'n. No. WO2005104996; Sep. 12, 2005; WIPO; Geneva, Switzerland; all pages.
LDR Medical, by its attorneys; Reply to Office Action in U.S. Appl. No. 12/391,086; Jan. 31, 2011; USPTO; Alexandria, Virgina; All Pages.
U.S. Patent & Trademark Office; Notice of Allowance in U.S. Appl. No. 12/391,086; Apr. 15, 2011; USPTO; Alexandria, Virgina; All Pages.
U.S. Patent & Trademark Office; Office Action in U.S. Appl. No. 12/391,086; Jul. 29, 2010; USPTO; Alexandria, Virgina; All Pages.
National Institute of Industrial Property (France); Preliminary Search Report in Fench Pub. No. FR2879436; Aug. 11, 2005; National Institute of Industrial Property (France); France; all pages.
U.S. Patent & Trademark Office; Notice of Allowance in U.S. Appl. No. 11/109,276; Dec. 8, 2009; USPTO; Alexandria, Virgina; All Pages.
World Intellectual Property Organization; International Preliminary Report on Patentability for PCT Pub'n. No. WO2006120505; Feb. 22, 2007; WIPO; Geneva, Switzerland; all pages.
World Intellectual Property Organization; International Search Report for PCT Pub'n. No. WO2006120505; Aug. 21, 2006; WIPO; Geneva, Switzerland; all pages.
World Intellectual Property Organization; Written Opinon of the International Searching Authority for PCT Pub'n. No. WO2006120505; Aug. 21, 2006; WIPO; Geneva, Switzerland; all pages.
LDR Medical, by its attorneys; Reply to Office Action in U.S. Appl. No. 12/360,050; Jun. 16, 2011; USPTO; Alexandria, Virgina; All Pages.
LDR Medical, by its attorneys; Reply to Office Action in U.S. Appl. No. 12/360,050; Mar. 6, 2012; USPTO; Alexandria, Virgina; All Pages.
U.S. Patent & Trademark Office; Notice of Allowance in U.S. Appl. No. 12/360,050; Mar. 26, 2012; USPTO; Alexandria, Virgina; All Pages.
U.S. Patent & Trademark Office; Office Action in U.S. Appl. No. 12/360,050; Dec. 17, 2010; USPTO; Alexandria, Virgina; All Pages.
U.S. Patent & Trademark Office; Office Action in U.S. Appl. No. 12/360,050; Sep. 6, 2011; USPTO; Alexandria, Virgina; All Pages.
National Institute of Industrial Property (France); Preliminary Search Report in Fench Pub. No. FR2887762; Dec. 21, 2005; National Institute of Industrial Property (France); France; all pages.
U.S. Patent & Trademark Office; Notice of Allowance in U.S. Appl. No. 11/180,868; Jul. 17, 2009; USPTO; Alexandria, Virgina; All Pages.
U.S. Patent & Trademark Office; Notice of Allowance in U.S. Appl. No. 11/180,868; Jul. 31, 2009; USPTO; Alexandria, Virgina; All Pages.
World Intellectual Property Organization; International Preliminary Report on Patentability for PCT Pub'n. No. WO2007000654; Jul. 19, 2007; WIPO; Geneva, Switzerland; all pages.
World Intellectual Property Organization; International Search Report for PCT Pub'n. No. WO2007000654; Mar. 14, 2007; WIPO; Geneva, Switzerland; all pages.
World Intellectual Property Organization; Written Opinon of the International Searching Authority for PCT Pub'n. No. WO2007000654; Mar. 14, 2007; WIPO; Geneva, Switzerland; all pages.
LDR Medical, by its attorneys; Reply to Office Action in U.S. Appl. No. 12/435,955; Apr. 11, 2012; USPTO; Alexandria, Virgina; All Pages.
U.S. Patent & Trademark Office; Office Action in U.S. Appl. No. 12/435,955; Oct. 11, 2011; USPTO; Alexandria, Virgina; All Pages.
LDR Medical, by its attorneys; Reply to Office Action in U.S. Appl. No. 11/341,007; Jun. 17, 2010; USPTO; Alexandria, Virgina; All Pages.
LDR Medical, by its attorneys; Reply to Office Action in U.S. Appl. No. 11/341,007; Oct. 13, 2009; USPTO; Alexandria, Virgina; All Pages.
National Institute of Industrial Property (France); Preliminary Search Report in Fench Pub. No. FR2891135; Jun. 27, 2006; National Institute of Industrial Property (France); France; all pages.
U.S. Patent & Trademark Office; Notice of Allowance in U.S. Appl. No. 11/341,007; Jul. 26, 2010; USPTO; Alexandria, Virgina; All Pages.
U.S. Patent & Trademark Office; Office Action in U.S. Appl. No. 11/341,007; Apr. 13, 2009; USPTO; Alexandria, Virgina; All Pages.
U.S. Patent & Trademark Office; Office Action in U.S. Appl. No. 11/341,007; Dec. 17, 2009; USPTO; Alexandria, Virgina; All Pages.
World Intellectual Property Organization; International Preliminary Report on Patentability for PCT Pub'n. No. WO2007034310; Aug. 14, 2007; WIPO; Geneva, Switzerland; all pages.
World Intellectual Property Organization; International Search Report for PCT Pub'n. No. WO2007034310; Feb. 13, 2007; WIPO; Geneva, Switzerland; all pages.
World Intellectual Property Organization; Written Opinon of the International Searching Authority for PCT Pub'n. No. WO2007034310; Feb. 13, 2007; WIPO; Geneva, Switzerland; all pages.
LDR Medical, by its attorneys; Reply to Office Action in U.S. Appl. No. 12/955,898; Apr. 19, 2012; USPTO; Alexandria, Virgina; All Pages.
U.S. Patent & Trademark Office; Office Action in U.S. Appl. No. 12/955,898; Mar. 19, 2012; USPTO; Alexandria, Virgina; All Pages.
LDR Medical, by its attorneys; Appeal Brief in U.S. Appl. No. 11/362,253; Apr. 9, 2012; USPTO; Alexandria, Virgina; All Pages.
LDR Medical, by its attorneys; Reply to Office Action in U.S. Appl. No. 11/362,253; Apr. 15, 2010; USPTO; Alexandria, Virgina; All Pages.
LDR Medical, by its attorneys; Reply to Office Action in U.S. Appl. No. 11/362,253; Dec. 20, 2010; USPTO; Alexandria, Virgina; All Pages.
National Institute of Industrial Property (France); Preliminary Search Report in Fench Pub. No. FR2893838; Aug. 4, 2006; National Institute of Industrial Property (France); France; all pages.
U.S. Patent & Trademark Office; Office Action in U.S. Appl. No. 11/362,253; Jun. 18, 2010; USPTO; Alexandria, Virgina; All Pages.
U.S. Patent & Trademark Office; Office Action in U.S. Appl. No. 11/362,253; Mar. 8, 2011; USPTO; Alexandria, Virgina; All Pages.
U.S. Patent & Trademark Office; Office Action in U.S. Appl. No. 11/362,253; Oct. 15, 2009; USPTO; Alexandria, Virgina; All Pages.
World Intellectual Property Organization; International Preliminary Report on Patentability for PCT Pub'n. No. WO2007063398; Nov. 12, 2007; WIPO; Geneva, Switzerland; all pages.
World Intellectual Property Organization; International Search Report for PCT Pub'n. No. WO2007063398; Jul. 13, 2007; WIPO; Geneva, Switzerland; all pages.
World Intellectual Property Organization; Written Opinon of the International Searching Authority for PCT Pub'n. No. WO2007063398; Jul. 13, 2007; WIPO; Geneva, Switzerland; all pages.
National Institute of Industrial Property (France); Preliminary Search Report in Fench Pub. No. FR2916956; Jan. 30, 2008; National Institute of Industrial Property (France); France; all pages.

(56) References Cited

OTHER PUBLICATIONS

U.S. Patent & Trademark Office; Office Action in U.S. Appl. No. 12/134,884; Jan. 31, 2012; USPTO; Alexandria, Virgina; All Pages.
World Intellectual Property Organization; International Preliminary Report on Patentability for PCT Pub'n. No. WO2008149223; Aug. 5, 2009; WIPO; Geneva, Switzerland; all pages.
World Intellectual Property Organization; International Search Report for PCT Pub'n. No. WO2008149223; Oct. 31, 2008; WIPO; Geneva, Switzerland; all pages.
World Intellectual Property Organization; Written Opinon of the International Searching Authority for PCT Pub'n. No. WO2008149223; Oct. 31, 2008; WIPO; Geneva, Switzerland; all pages.
World Intellectual Property Organization; International Search Report for PCT Pub'n. No. WO2011080535; Jan. 24, 2011; WIPO; Geneva, Switzerland; all pages.
LDR Medical, by its attorneys; Appeal Brief in U.S. Appl. No. 11/676,237; Oct. 17, 2011; USPTO; Alexandria, Virgina; All Pages.
LDR Medical, by its attorneys; Reply to Office Action in U.S. Appl. No. 11/676,237; Jun. 18, 2010; USPTO; Alexandria, Virgina; All Pages.
LDR Medical, by its attorneys; Reply to Office Action in U.S. Appl. No. 11/676,237; Sep. 21, 2009; USPTO; Alexandria, Virgina; All Pages.
U.S. Patent & Trademark Office; Office Action in U.S. Appl. No. 11/676,237; Dec. 18, 2009; USPTO; Alexandria, Virgina; All Pages.
U.S. Patent & Trademark Office; Office Action in U.S. Appl. No. 11/676,237; Feb. 16, 2012; USPTO; Alexandria, Virgina; All Pages.
U.S. Patent & Trademark Office; Office Action in U.S. Appl. No. 11/676,237; Sep. 15, 2010; USPTO; Alexandria, Virginia; All Pages.
U.S. Patent & Trademark Office; Office Action in U.S. Appl. No. 12/527,373; Dec. 12, 2011; USPTO; Alexandria, Virgina; All Pages.
World Intellectual Property Organization; International Preliminary Report on Patentability for PCT Pub'n. No. WO2008099277; May 29, 2009; WIPO; Geneva, Switzerland; all pages.
World Intellectual Property Organization; International Search Report for PCT Pub'n. No. WO2008099277; Nov. 7, 2008; WIPO; Geneva, Switzerland; all pages.
World Intellectual Property Organization; Written Opinon of the International Searching Authority for PCT Pub'n. No. WO2008099277; Nov. 7, 2008; WIPO; Geneva, Switzerland; all pages.
Apparatus and Method for Fusing Opposing Spinal Vertebrae, Bramlet, Dale G. et al., U.S. Appl. No. 09/635,436, filed Aug. 11, 2000.
Intervertebral nucleus prosthesis and surgical procedure for implanting the same, Gau, Michel, U.S. Appl. No. 10/060,862, filed Jan. 30, 2002.
Intersomatic cage with unified grafts, Huppert, Jean, U.S. Appl. No. 10/276,712, filed Mar. 26, 2003.
Spinal Osteosynthesis Device and Preparation Method, Beaurain, Jacques et al., U.S. Appl. No. 10/473,999, filed Apr. 12, 2004.
Intervertebral Disc Prosthesis and Fitting Tools, Beaurain, Jacques et al., U.S. Appl. No. 10/476,565, filed Jun. 8, 2004.
Vertebral Cage Device With Modular Fixation, Louis, Christian et al., U.S. Appl. No. 10/483,563, filed May 21, 2004.
Progressive approach osteosynthesis device and preassembly method, Delecrin, Joel et al., U.S. Appl. No. 10/492,753, filed Aug. 9, 2004.
Plate for osteosynthesis device and method of preassembling such device Delecrin, Joel et al., U.S. Appl. No. 10/492,827, filed Jul. 15, 2004.
Osseous anchoring device for a prosthesis, Huppert, Jean et al., U.S. Appl. No. 10/494,418, filed Jul. 22, 2004.
Implant for Osseous Anchoring with Polyaxial Head, Beaurain, Jacques et al., U.S. Appl. No. 10/498,234, filed Dec. 7, 2004.
Intervertebral Disk Prosthesis, Beaurain, Jacques et al., U.S. Appl. No. 10/533,846, filed Nov. 11, 2005.
Osseous anchoring implant with a polyaxial head and method for installing the implant, Renaud, Christian et al., U.S. Appl. No. 10/570,080, filed Jun. 9, 2006.
Device and method for sectioning a vertebral lamina, Mangione, Paolo, U.S. Appl. No. 10/575,065, filed May 30, 2006.
Intervertebral Disc Prosthesis, Hovorka, Istvan et al., U.S. Appl. No. 11/051,710, filed Feb. 4, 2005.
Intervertebral Disc Prosthesis, Zeegers, M. Willem, U.S Appl. No. 11/098,266, filed Apr. 4, 2005.
Intervertebral Disc Prosthesis, Zeegers, M. Willem, U.S. Appl. No. 11/109,276, filed Apr. 18, 2005.
Instrumentation and Methods for Inserting an Intervertebral Disc Prosthesis, Dinville, Herve, U.S. Appl. No. 11/180,868, filed Jul. 13, 2005.
Intervertebral Disc Prosthesis, Rashbaum, Ralph et al., U.S. Appl. No. 11/341,007, filed Jan. 27, 2006.
Intervertebral Disc Prosthesis and Instrumentation for Insertion of the Prosthesis Between the Vertebrae, Rashbaum, Ralph et al., U.S. Appl. No. 11/362,253, filed Feb. 24, 2006.
Transforanimal intersomatic cage for an intervertebral fusion graft and an instrument for implanting the cage, Davis, Reginald James et al., U.S. Appl. No. 11/378,165, filed Mar. 17, 2006.
Intervertebral nucleus prosthesis and surgical procedure for implanting the same, Gau, Michel, U.S. Appl. No. 11/390,711, filed Mar. 27, 2006.
Intervertebral disc prosthesis insertion assemblies, Jodaitis, Alexandre et al., U.S. Appl. No. 11/676,237, filed Feb. 16, 2007.
Intersomatic cage with unified grafts, Huppert, Jean, U.S. Appl. No. 11/767,386, filed Jun. 22, 2007.
Modular intervertebral prosthesis, Vila, Thierry et al., U.S. Appl. No. 11/874,144, filed Oct. 17, 2007.
Vertebral Support Device, Cho, Paul et al., U.S. Appl. No. 11/958,285, filed Dec. 17, 2007.
Intervertebral disc prosthesis, surgical methods, and fitting tools, Beaurain, Jacques et al., U.S. Appl. No. 12/025,677, filed Feb. 4, 2008.
Intersomatic cage, intervertebral prosthesis, anchoring device and implantation instruments, Allain, Jerome et al., U.S. Appl. No. 12/134,884, filed Jun. 6, 2008.
Transverse spinal linking device and system, Paul, Cho et al., U.S. Appl. No. 12/172,074, filed Jul. 11, 2008.
Transforaminal intersomatic cage for an intervertebral fusion graft and an instrument for implanting the cage, Davis, Reginald James et al., U.S. Appl. No. 12/279,664, filed Apr. 22, 2009.
Intervertebral Disc Prosthesis, Zeegers, M. Willem U.S. Appl. No. 12/360,050, filed Jan. 26, 2009.
Intervertebral Disc Prosthesis, Zeegers, M. Willem, U.S. Appl. No. 12/391,086, filed Feb. 23, 2009.
Spinal Osteosynthesis Device and Preparation Method, Beaurain, Jacques et al., U.S. Appl. No. 12/409,327, filed Mar. 23, 2009.
Intervertebral disc prosthesis, Beaurain, Jacques et al., U.S. Appl. No. 12/424,364, filed Apr. 15, 2009.
Vertebral Cage Device With Modular Fixation, Louis, Christian et al., U.S. Appl. No. 12/430,768, filed Apr. 27, 2009.
Instrumentation and Methods for Inserting an Intervertebral Disc Prosthesis, Dinville, Herve, U.S. Appl. No. 12/435,955, filed May 5, 2009.
Intervertebral disc prosthesis insertion assemblies, Jodaitis, Alexandre et al., U.S. Appl. No. 12/527,373, filed Mar. 19, 2010.
Intervertebral Disc Prosthesis, Rashbaum, Ralph et al., U.S. Appl. No. 12/955,898, filed Nov. 29, 2010.
Instruments and Methods for Removing Fixation Devices from Intervertebral Implants, Dinville, Herve et al., U.S. Appl. No. 13/158,761, filed Jun. 13, 2011.
Intervertebral Disc Prosthesis, Zeegers, M. Willem, U.S. Appl. No. 13/215,123, filed Aug. 22, 2011.
Interspinous Implant and Implantation Instrument, Dinville, Hervéet al. U.S. Appl. No. 13/369,650, filed Feb. 9, 2012.
Vertebral Cage Device With Modular Fixation, Louis, Christian et al. U.S. Appl. No. 13/438,352, filed Apr. 3, 2012.
Plate for osteosynthesis device and method of preassembling such device, Delecrin, Joel et al. U.S. Appl. No. 13/454,927, filed Apr. 24, 2012.

(56) References Cited

OTHER PUBLICATIONS

Anchoring Device and System for an Intervertebral Implant, Intervertebral Implant and Implantation Instrument, Dinville, Hervé et al. U.S. Appl. No. 13/520,041, filed Nov. 26, 2012.
Anchoring Device and System for an Intervertebral Implant, Intervertebral Implant and Implantation Instrument, Dinville, Hervé et al. U.S. Appl. No. 13/538,078, filed Jun. 29, 2012.
Transforaminal intersomatic cage for an intervertebral fusion graft and an instrument for implanting the cage, Davis, Reginald James et al., U.S. Appl. No. 13/585,063, filed Aug. 14, 2012.
Intervertebral Disc Prosthesis, Zeegers, M. Willem, U.S. Appl. No. 13/603,043, filed Sep. 4, 2012.
Intervertebral Disk Prosthesis, Beaurain, Jacques et al., U.S. Appl. No. 13/616,448, filed Sep. 14, 2012.
Intervertebral Disc Prosthesis and Instrumentation for Insertion of the Prosthesis Between the Vertebrae, Rashbaum, Ralph et al., U.S. Appl. No. 13/620,797, filed Sep. 15, 2012.
Intersomatic cage, intervertebral prosthesis, anchoring device and implantation instruments, Allain, Jerome et al., U.S. Appl. No. 13/732,244, filed Dec. 31, 2012.
Anchoring device and system for an intervertebral implant, intervertebral implant and implantation instrument, Chataigner, Hervé et al., U.S. Appl. No. 13/774,547, filed Feb. 22, 2013.
Transforanimal intersomatic cage for an intervertebral fusion graft and an instrument for implanting the cage, Davis, Reginald James et al., U.S. Appl. No. 13/854,808, filed Apr. 1, 2013.
Spinal Osteosynthesis Device and Preparation Method, Beaurain, Jacques et al. U.S. Appl. No. 13/873,190 filed Apr. 29, 2013.
Instrumentation and Methods for Inserting an Intervertebral Disc Prosthesis, Dinville, Herve U.S. Appl. No. 13/892,933, filed May 13, 2013.
Intervertebral disc prosthesis insertion assemblies, Jodaitis, Alexandre et al. U.S. Appl. No. 13/919,704, filed Jun. 17, 2013.
Interspinous Implant and Implantation Instrument, Dinville, Hervé et al. U.S. Appl. No. 14/130,286, filed Jul. 3, 2014.
Intersomatic cage with unified grafts, Huppert, Jean U.S. Appl. No. 14/149,357, filed Jan. 7, 2014.
Nucleus Prostheses, Vila, Thierry et al., U.S. Appl. No. 14/159,161, filed Jan. 20, 2014.
Intervertebral disc prosthesis insertion assemblies, Jodaitis, Alexandre et al., U.S. Appl. No. 14/242,177, filed Apr. 1, 2014.
Vertebral implant, vertebral fastening device of the implant and implant instrumentation, Dinville, Hervé et al. U.S. Appl. No. 14/246,442 filed Apr. 7, 2014.
Interspinous Implant and Implantation Instrument, Dinville, Hervé et al. U.S. Appl. 14/252,754, filed Apr. 14, 2014.
Anchoring device for a spinal implant, spinal implant and implantation instrumentaton, Hervé, Chataigner et al., U.S. Appl. No. 14/252,582, filed Apr. 15, 2014.
Intervertebral Disc Prosthesis, Beaurain, Jacques et al., U.S. Appl. No. 14/306,785, filed Jun. 17, 2014.
Intervertebral Disc Prosthesis and Instrumentation for Insertion of the Prosthesis Between the Vertebrae, Rashbaum, Ralph et al., U.S. Appl. No. 14/325,317, filed Jul. 7, 2014.
Anchoring device and system for an intervertebral implant, intervertebral implant and implantation instrument, Hervé, Chataigner et al., U.S. Appl. No. 14/380,714, filed Aug. 23, 2014.
Osseous anchoring implant with a polyaxial head and method for installing the implant, Renaud, Christian et al., U.S. Appl. No. 14/497,321, filed Sep. 26, 2014.
Intervertebral Disc Prothesis, Hovorka, Istvan et al., U.S. Appl. No. 14/513,818, file Oct. 14, 2014.
National Institute of Industrial Property (France); Search Report for Pub'n No. FR2827156, App. No. FR0109381; Apr. 5, 2002; National Institute of Industrial Property (France); France; all pages.
World Intellectual Property Organization; International Preliminary Examination Report for International App. No. PCT/IB02/03390, PCT Pub'n. No. W003005939; Nov. 6, 2003; WIPO; Geneva, Switzerland; all pages.

World Intellectual Property Organization; International Search Report for International App. No. PCT/IB02/03390, PCT Pub'n No. W003005939; Mar. 3, 2003; WIPO; Geneva, Switzerland; all pages.
European Patent Office; Notice of Intent to Grant Patent for App. No. 02784881, Pub'n No. EP1406563; Aug. 26, 2010; EPO; Munich, Germany; all pages.
European Patent Office; Office Action for App. No. 02784881, Pub'n No. EP1406563; Mar. 13, 2009; EPO; Munich, Germany; all pages.
European Patent Office; Office Action for App. No. 02784881, Pub'n No. EP1406563; Aug. 4, 2009; EPO; Munich, Germany; all pages.
LDR Medical, by its attorneys; Reply to Office Action for App. No. 02784881, Pub'n No. EP1406563; Jul. 22, 2009; EPO; Munich, Germany; all pages.
LDR Medical, by its attorneys; Reply to Office Action for App. No. 02784881, Pub'n No. EP1406563; Oct. 14, 2009; EPO; Munich, Germany; all pages.
LDR Medical, by its attorneys; Amendment for Pub'n No. EP2113228, Application No. EP09009533; Apr. 26, 2010; EPO; Munich, Germany; all pages.
European Patent Office; Search Report for Pub'n No. EP2113228, Application No. EP09009533; Oct. 6, 2009; EPO; Munich, Germany; all pages.
European Patent Office; Search Report for Pub'n No. EP2340788, Application No. EP11157596; Jun. 8, 2011; EPO; Munich, Germany; all pages.
European Patent Office; Notice of Intention to Grant a European Patent for Pub'n No. EP1711133; Oct. 22, 2010; EPO; Munich, Germany; all pages.
European Patent Office; Office Action for Pub'n No. EP1711133; Mar. 2, 2009; EPO; Munich, Germany; all pages.
LDR Medical, by its attorneys; Reply to Office Action for Pub'n No. EP1711133; Jul. 22, 2009; EPO; Munich, Germany; all pages.
European Patent Office; Office action and search report in Application No. 05857774, Pub. No. EP1845903; May 6, 2009; European Patent Office; Munich, Germany; All Pages.
European Patent Office; Office action and search report in Application No. 05857774, Pub. No. EP1845903; Apr. 11, 2011; European Patent Office; Munich, Germany; All Pages.
LDR Medical, by its attorneys; Amendments and Reply in European Patent Application No. 05857774, Pub. No. EP1845903; Nov. 13, 2009; European Patent Office; Munich, Germany; All Pages.
LDR Medical, by its attorneys; Amendments and Reply in European Patent Application No. 05857774, Pub. No. EP1845903; Oct. 11, 2011; European Patent Office; Munich, Germany; All Pages.
European Patent Office; Office action and search report in Application No. 11165170, Pub. No. EP2363080; Jul. 21, 2011; European Patent Office; Munich, Germany; All Pages.
European Patent Office; Office action in Application No. 11165170, Pub. No. EP2363080; May 15, 2012; European Patent Office; Munich, Germany; All Pages.
LDR Medical, by its attorneys; Amendments and Reply in European Patent Application No. 11165170, Pub. No. EP2363080; Mar. 6, 2012; European Patent Office; Munich, Germany; All Pages.
LDR Medical, by its attorneys; Chapter II amendments for PCT Pub'n. No. W02006120505, App. No. PCT/IB2005/004093; Oct. 30, 2006; WIPO; Geneva, Switzerland; All Pages.
National Institute of Industrial Property (France); Search Report for Pub'n No. FR2897259, App. No. FR0601315; Oct. 11, 2006; National Institute of Industrial Property (France); France; all pages.
World Intellectual Property Organization; International Preliminary Report on Patentability for International App. No. PCT/IB2007/000367, PCT Pub'n No. W02007093900; Feb. 5, 2008; WIPO; Geneva, Switzerland; all pages.
World Intellectual Property Organization; International Search Report and Written Opinon of the International Searching Authority for International App. No. PCT/IB2007/000367, PCT Pub'n No. W02007093900; Oct. 22, 2007; WIPO; Geneva, Switzerland; all pages.
LDR Medical, by its attorneys; Amendment for Pub'n No. EP1996127, Application No. EP07733892; Nov. 26, 2008; EPO; Munich, Germany; all pages.

(56) References Cited

OTHER PUBLICATIONS

LDR Medical, by its attorneys; Amendment for Pub'n No. EP2162098, Application No. EP08762820; Jan. 6, 2010; EPO; Munich, Germany; all pages.
European Patent Office; Office Action for Pub'n No. EP2162098, Application No. EP08762820; Jan. 17, 2012; EPO; Munich, Germany; all pages.
LDR Medical, by its attorneys; Reply to Office Action for Pub'n. No. EP2162098, Application No. EP08762820; Jul. 27, 2012; EPO; Munich, Germany; all pages.
LDR Medical, by its attorneys; Amendment for International App. No. PCT/IB2008/001484, Pub'n No. W02008149223; May 13, 2009; WIPO; Geneva, Switzerland; all pages.
World Intellectual Property Organization; International Preliminary Report on Patentability for International App. No. PCT/IB2009/008048, PCT Pub'n No. W02011080535; Apr. 18, 2012; WIPO; Geneva, Switzerland; all pages.
World Intellectual Property Organization; International Search Report and Written Opinion of the International Searching Authority for International App. No. PCT/IB2009/008048, PCT Pub'n. No. W02011080535; Feb. 2, 2011; WIPO; Geneva, Switzerland; all pages.
LDR Medical, by its attorneys; Amendment for International App. No. PCT/IB2009/008048, Pub'n No. W02011080535; Apr. 2, 2012; WIPO; Geneva, Switzerland; all pages.
LDR Medical, by its attorneys; Demand for International App. No. PCT/IB2009/008048, PCT Pub'n No. W02011080535; Apr. 19, 2011; WIPO; Geneva, Switzerland; all pages.
World Intellectual Property Organization; Interview Summary for International App. No. PCT/IB2009/008048, PCT Pub'n No. W02011080535; Feb. 14, 2012; WIPO; Geneva, Switzerland; all pages.
National Institute of Industrial Property (France); Search Report in Fench Pub. No. FR2987256, App. No. FR1251733; Dec. 5, 2012; National Institute of Industrial Property (France); France; all pages.
World Intellectual Property Organization; International Preliminary Report on Patentability for International App. No. PCT/EP2013/053622, PCT Pub'n No. WO 2013/124453; Jul. 11, 2014; WIPO; Geneva, Switzerland; all pages.
World Intellectual Property Organization; International Search Report and Written Opinion of the International Searching Authority for International App. No. PCT/EP2013/053622, PCT Pub'n No. W02013124453; May 29, 2013; WIPO; Geneva, Switzerland; all pages.
LDR Medical, by its attorneys; Response to International Search Report for International App. No. PCT/EP2013/053622, International Application No. PCT/EP2013/053622; Dec. 18, 2013; WIPO; Geneva, Switzerland; all pages.
U.S. Patent & Trademark Office; Notice of Allowance in Application U.S. Appl. No. 10/483,563; Jun. 19, 2009; USPTO; Alexandria, Virgina; All Pages.
U.S. Patent & Trademark Office; Notice of Allowance in Application U.S. Appl. No. 10/483,563; Jun. 5, 2009; USPTO; Alexandria, Virgina; All Pages.
LDR Medical, by its attorneys; Reply to Office Action in Application U.S. Appl. No. 10/483,563; Apr. 28, 2009; USTPO; Alexandria, Virgina; All Pages.
U.S. Patent & Trademark Office; Office Action in Application U.S. Appl. No. 10/483,563; Oct. 28, 2008; USPTO; Alexandria, Virgina; All Pages.
LDR Medical, by its attorneys; Reply to Office Action in U.S. Appl. No. 10/483,563; Jul. 31, 2008; USPTO; Alexandria, Virgina; All Pages.
U.S. Patent & Trademark Office; Office Action in U.S. Appl. No. 10/483,563; Jan. 31,2008; USPTO; Alexndria, Virgina; All Pages.
LDR Medical, by its attorneys; Reply to Office Action in U.S. Appl. No. 10/483,563; Nov. 19, 2007; USPTO; Alexandria, Virgina; All Pages.
U.S. Patent & Trademark Office; Office Action in U.S. Appl. No. 10/483,563; Oct. 30, 2007; USPTO; Alexandria, Virgina; All Pages.
LDR Medical, by its attorneys; Reply to Office Action in U.S. Appl. No. 10/483,563; Aug. 21, 2007; USPTO; Alexandria, Virgina; All Pages.
U.S. Patent & Trademark Office; Office Action in Application U.S. Appl. No. 10/483,563; Feb. 21, 2007; USPTO; Alexandria, Virgina; All Pages.
U.S. Patent & Trademark Office; Notice of Allowance in Application U.S. Appl. No. 12/430,768; Jan. 19, 2012; USPTO; Alexandria, Virgina; All Pages.
U.S. Patent & Trademark Office; Notice of Allowance in Application U.S. Appl. No. 12/430,768; Jan. 11, 2012; USPTO; Alexandria, Virgina; All Pages.
LDR Medical, by its attorneys; Reply to Office Action in Application U.S. Appl. No. 12/430,768; Dec. 14, 2011; USPTO; Alexandria, Virgina; All Pages.
U.S. Patent & Trademark Office; Office Action in Application U.S. Appl. No. 12/430,768; Jun. 14, 2011; USPTO; Alexandria, Virgina; All Pages.
U.S. Patent & Trademark Office; Office Action in Application U.S. Appl. No. 13438352; Aug. 14, 2014; USPTO; Alexandria, Virgina; All Pages.
U.S. Patent & Trademark Office; Notice of Allowance in Application U.S. Appl. No. 12/279,664; May 29, 2012; USPTO; Alexandria, Virgina; All Pages.
U.S. Patent & Trademark Office; Notice of Allowance and Interview Summary in Application U.S. Appl. No. 12/279,664; Apr. 11, 2012; USPTO; Alexandria, Virgina; All Pages.
LDR Medical, by its attorneys; Reply to Office Action in Application U.S. Appl. No. 12/279,664; Mar. 14, 2012; USPTO; Alexandria, Virgina; All Pages.
U.S. Patent & Trademark Office; Office Action in U.S. Appl. No. 12/279,664; Sep. 14, 2011; USPTO; Alexandria, Virgina; All Pages.
U.S. Patent & Trademark Office; Notice of Allowance in U.S. Appl. No. 12/279,664; Jul. 24, 2011; USPTO; Alexandria, Virgina; All Pages.
U.S. Patent & Trademark Office; Notice of Allowance in U.S. Appl. No. 12/279,664; Aug. 2, 2012; USPTO; Alexandria, Virgina; All Pages.
LDR Medical, by its attorneys; Reply to Office Action in U.S. Appl. No. 12/279,664; Jul. 6, 2012; USPTO; Alexandria, Virgina; All Pages.
U.S. Patent & Trademark Office; Notice of Allowance in U.S. Appl. No. 13/616,448; Feb. 7, 2014; USPTO; Alexandria, Virgina; All Pages.
U.S. Patent & Trademark Office; Office Action in U.S. Appl. No. 13/616,448; Aug. 22, 2013; USPTO; Alexandria, Virgina; All Pages.
U.S. Patent & Trademark Office; Notice of Allowance in U.S. Appl. No. 12/360,050; May 18, 2012; USPTO; Alexandria, Virgina; All Pages.
U.S. Patent & Trademark Office; Notice of Allowance in U.S. Appl. No. 12/360,050; Jul. 6, 2012; USPTO; Alexandria, Virgina; All Pages.
U.S. Patent & Trademark Office; Notice of Allowance in U.S. Appl. No. 12/360,050; Aug. 2, 2012; USPTO; Alexandria, Virgina; All Pages.
U.S. Patent & Trademark Office; Office Action in Application U.S. Appl. No. 13/603,043; Apr. 9, 2013; USPTO; Alexandria, Virgina; All Pages.
U.S. Patent & Trademark Office; Office Action in U.S. Appl. No. 13/603,043; Nov. 21,2012; USPTO; Alexandria, Virgina; All Pages.
LDR Medical, by its attorneys; Reply to Office Action in U.S. Appl. No. 13/603,043; Oct. 9, 2013; USPTO; Alexandria, Virgina; All Pages.
U.S. Patent & Trademark Office; Notice of Allowance in U.S. Appl. No. 12,134,884, Nov. 1, 2012; USPTO; Alexandria, Virgina; All Pages.
LDR Medical, by its attorneys; Reply to Office Action in U.S. Appl. No. 12,134,884, Jul. 31, 2012; USPTO; Alexandria, Virgina; All Pages.
U.S. Patent & Trademark Office; Office Action in U.S. Appl. No. 12,134,884, Sep. 19, 2014; USPTO; Alexandria, Virgina; All Pages.

(56) References Cited

OTHER PUBLICATIONS

LDR Medical, by its attorneys; Reply to Office Action in U.S. Appl. No. 12,134,884, Jul. 30, 2014; USPTO; Alexandria, Virgina; All Pages.
U.S. Patent & Trademark Office; Office Action in Application U.S. Appl. No. 13732244; Apr. 30, 2014; USPTO; Alexandria, Virgina; All Pages.
U.S. Patent & Trademark Office; Office Action in Application U.S. Appl. No. 13520041; Oct. 6, 2014; USPTO; Alexandria, Virgina; All Pages.
LDR Medical, by its attorneys; Reply to Office Action in Application U.S. Appl. No. 13520041; Sep. 19, 2014; USPTO; Alexandria, Virgina; All Pages.
U.S. Patent & Trademark Office; Office Action in Application U.S. Appl. No. 13520041; Mar. 20, 2014; USPTO; Alexandria, Virgina; All Pages.
U.S. Patent & Trademark Office; Office Action in Application U.S. Appl. No. 13538078; May 12, 2014; USPTO; Alexandria, Virgina; All Pages.
U.S. Patent & Trademark Office; Examiner's Interview Summary in Application U.S. Appl. No. 13774547; Jul. 3, 2014; USPTO; Alexandria, Virgina; All Pages.
U.S. Patent & Trademark Office; Notice of Allowance in Application U.S. Appl. No. 13774547; Jul. 3, 2014; USPTO; Alexandria, Virgina; All Pages.
U.S. Patent & Trademark Office; Interview Summary in Application U.S. Appl. No. 13158761; Oct. 31, 2012; USPTO; Alexandria, Virgina; All Pages.
U.S. Patent & Trademark Office; Interview Summary in Application U.S. Appl. No. 13158761; Aug. 1, 2013; USPTO; Alexandria, Virgina; All Pages.
U.S. Patent & Trademark Office; Office Action in Application U.S. Appl. No. 13158761; Oct. 17, 2012; USPTO; Alexandria, Virgina; All Pages.
U.S. Patent & Trademark Office; Office Action in U.S. Appl. No. 13/158,761; Feb. 28, 2013; USPTO; Alexandria, Virgina; All Pages.
U.S. Patent & Trademark Office; Office Action in U.S. Appl. No. 13/158,761; Aug. 14, 2013; USPTO; Alexandria, Virgina; All Pages.
LDR Medical, by its attorneys; Reply to Office Action in U.S. Appl. No. 13/158,761; Nov. 19, 2012; USPTO; Alexandria, Virgina; All Pages.
LDR Medical, by its attorneys; Reply to Office Action in U.S. Appl. No. 13/158,761; Jul. 29, 2013; USPTO; Alexandria, Virgina; All Pages.
LDR Medical, by its attorneys; Reply to Office Action in U.S. Appl. No. 13/158,761; Nov. 14, 2013; USPTO; Alexandria, Virgina; All Pages.
LDR Medical; Mc+ Le choix de l'ancrage; Sep. 19, 2004; LDR Medical; France; all pages.
U.S. Patent & Trademark Office; Office Action in U.S. Appl. No. 12/025,677; Jun. 29, 2012; USPTO; Alexandria, Virgina; All Pages.
U.S. Patent & Trademark Office; Office Action in U.S. Appl. No. 12/025,677; Jun. 20, 2013; USPTO; Alexandria, Virgina; All Pages.
U.S. Patent & Trademark Office; Reply to Office Action in U.S. Appl. No. 12/025,677; Feb. 19, 2014; USPTO; Alexandria, Virgina; All Pages.
LDR Medical, by its attorneys; Reply to Office Action in U.S. Appl. No. 12/025,677; Dec. 29, 2012; USPTO; Alexandria, Virgina; All Pages.
LDR Medical, by its attorneys; Reply to Office Action in U.S. Appl. No. 12/025,677; Dec. 20, 2013; USPTO; Alexandria, Virgina; All Pages.
LDR Medical, by its attorneys; Appeal Brief in U.S. Appl. No.11/051,710; Jan. 15, 2013; USPTO; Alexandria, Virgina; All Pages.
U.S. Patent & Trademark Office; Notice of Allowance in U.S. Appl. No. 11051710; Apr. 11, 2013; USPTO; Alexandria, Virgina; All Pages.
LDR Medical, by its attorneys; Request for Continued Examination in U.S. Appl. No. 11/051,710; Jul. 11, 2013; Uspto; Alexandria, Virgina; All Pages.
U.S. Patent & Trademark Office; Office Action in U.S. Appl. No. 13/215,123; Nov. 20, 2012; USPTO; Alexandria, Virgina; All Pages.
U.S. Patent & Trademark Office; Office Action in U.S. Appl. No. 13/215,123; Jul. 24, 2013; USPTO; Alexandria, Virgina; All Pages.
U.S. Patent & Trademark Office; Office Action in U.S. Appl. No. 13/215,123; Nov. 18, 2013; USPTO; Alexandria, Virgina; All Pages.
LDR Medical, by its attorneys; Reply to Office Action in U.S. Appl. No. 13/215,123; Mar. 20, 2012; USPTO; Alexandria, Virgina; All Pages.
LDR Medical, by its attorneys; Reply to Office Action in U.S. Appl. No. 13/215,123; Oct. 24, 2013; USPTO; Alexandria, Virgina; All Pages.
LDR Medical, by its attorneys; Reply to Office Action in U.S. Appl. No. 13/215,123; Nov. 11, 2013; USPTO; Alexandria, Virgina; All Pages.
LDR Medical, by its attorneys; Terminal Disclaimer in U.S. Appl. No. 13/215,123; Mar. 20, 2013; USPTO; Alexandria, Virgina; All Pages.
U.S. Patent & Trademark Office; Notice of Allowance in U.S. Appl. No. 12/435,955; Jan. 16, 2013; USPTO; Alexandria, Virgina; All Pages.
U.S. Patent & Trademark Office; Office Action in U.S. Appl. No. 12/435,955; Jul. 23, 2012; USPTO; Alexandria, Virgina; All Pages.
LDR Medical, by its attorneys; Reply to Office Action in U.S. Appl. No. 12/435,955; Dec. 24, 2012; USPTO; Alexandria, Virgina; All Pages.
U.S. Patent & Trademark Office; Office Action in U.S. Appl. No. 13/892,933; Jan. 2, 2014; USPTO; Alexandria, Virgina; All Pages.
U.S. Patent & Trademark Office; Examiners Answer to Appeal Brief in U.S. Appl. No. 11/362,253; Jun. 20, 2012; USPTO; Alexandria, Virgina; All Pages.
LDR Medical, by its attorneys; Reply Brief in U.S. Appl. No. 11/362,253; Aug. 20, 2012; USPTO; Alexandria, Virgina; All Pages.
U.S. Patent & Trademark Office; Notice of Allowance in U.S. Appl. No. 13/620,797; filed Jan. 29, 2014; USPTO; Alexandria, Virgina; All pages.
U.S. Patent & Trademark Office; Office Action in U.S. Appl. No. 13/620,797; filed Jul. 5, 2013; USPTO; Alexandria, Virgina; All pages.
LDR Medical, by its attorneys; Reply to Office Action in U.S. Appl. No. 13/620,797; filed Nov. 5, 2013; USPTO; Alexandria, Virgina; All Pages.
U.S. Patent & Trademark Office; Notice of Allowance in U.S. Appl. No. 11/676,237; filed Feb. 20, 2013; USPTO; Alexandria, Virgina; All Pages.
U.S. Patent & Trademark Office; Office Action in U.S. Appl. No. 11/676,237; filed Nov. 6, 2012; USPTO; Alexandria, Virgina; All Pages.
LDR Medical, by its attorneys; Reply to Office Action in U.S. Appl. No. 11/676,237; filed Jul. 16, 2012; USPTO; Alexandria, Virgina; All Pages.
LDR Medical, by its attorneys; Reply to Office Action in U.S. Appl. No. 11/676,237; filed Feb. 6, 2013; USPTO; Alexandria, Virgina; All Pages.
U.S. Patent & Trademark Office; Office Action in U.S. Appl. No. 13/197,704; filed Oct. 31, 2013; USPTO; Alexandria, Virgina; All Pages.
LDR Medical, by its attorneys; Reply to Office Action in U.S. Appl. No. 13/919,704; filed Jan. 31, 2014; USPTO; Alexandria, Virgina; All Pages.
LDR Medical, by its attorneys; Appeal Brief in U.S. Appl. No. 12/527,373; filed Apr. 24, 2013; USPTO; Alexandria, Virgina; All Pages.
U.S. Patent & Trademark Office; Interview Summary in U.S. Appl. No. 12/527,373; filed Aug. 30, 2013; USPTO; Alexandria, Virgina; All Pages.
LDR Medical, by its attorneys;Interview Summary in U.S. Appl. No. 12/527,373; filed Jan. 31, 2014; USPTO; Alexandria, Virgina; All Pages.
U.S. Patent & Trademark Office; Notice of Allowance in U.S. Appl. No. 12/527,373; filed Aug. 30, 2013; USPTO; Alexandria, Virgina; All Pages.

(56) References Cited

OTHER PUBLICATIONS

U.S. Patent & Trademark Office; Notice of Allowance in U.S. Appl. No. 12/527,373; Dec. 24, 2013; USPTO; Alexandria, Virgina; All Pages.

U.S. Patent & Trademark Office; Office Action in U.S. Appl. No. 12/527,373; Sep. 24, 2012; USPTO; Alexandria, Virgina; All Pages.

LDR Medical, by its attorneys; Request for Continued Examination in U.S. Appl. No. 12/527,373; Dec. 2, 2013; USPTO; Alexandria, Virgina; All Pages.

LDR Medical, by its attorneys; Reply to Office Action in U.S. Appl. No. 12/527,373; Jun. 21, 2012; USPTO; Alexandria, Virgina; All Pages.

\* cited by examiner

INTERVERTEBRAL DISC PROSTHESIS

CROSS REFERENCE TO RELATED APPLICATIONS

This application is a continuation of U.S. application Ser. No. 11/341,007 filed Jan. 27, 2006, issuing as U.S. Pat. No. 7,842,088 on Nov. 30, 2010, which claims priority from Application No. FR 0509740 filed in France on Sep. 23, 2005, all of which are incorporated herein by reference.

BACKGROUND

The invention relates to an intervertebral disc prosthesis, intended to be substituted for fibrocartilaginous discs providing the liaison between the vertebrae of the spinal column.

Different types of intervertebral disc prostheses are known in the prior art. Numerous prostheses, such as for example those described in the applications WO 02 089 701 and WO 2004/041129, are constituted of a lower plate and an upper plate creating a cage articulated about a central core. Other prostheses like those disclosed in the U.S. Pat. No. 5,676,701 and in the application WO 03/059212 A1, for example, only comprise a lower plate and an upper plate articulated about themselves by means of a surface of articulation. These articulated prostheses have the advantage of offering the patient bearing the prosthesis a freedom of movement, by allowing the plates to tilt and/or rotate in relation to each other. The prostheses comprising a central core, movable between the plates, have the added advantage of allowing a spontaneous positioning of the core in the ideal position for absorbing the constraints imposed on the prosthesis. In these prostheses known in the prior art, the anterior, posterior and lateral edges of a plate are located on the same vertical axis as the corresponding edge of the other plate. This shape of the prosthesis is normally due to the plates being of identical size and that their respective axes of articulation are joined (coaxially), so as to facilitate the movements of the patient and to allow the correction of possible positioning defects. However, these prostheses have the inconvenience of not being perfectly suited to the morphology of the spinal column. Indeed, the posterior edges of two adjacent vertebrae are often slightly off-set to each other. Thus, the prostheses known in the prior art are difficult to properly implant. Additionally, at rest, due to the natural off-setting of the vertebrae and the anchoring of the plates in the vertebrae, the different parts of the prosthesis are under constraint in an undesirable position as it restricts freedom of movement of these parts of the prosthesis. This inconvenience will be diminished through the use of a movable core between the plates, but the possible movements of the core will be restricted and its capacity to position itself so as to absorb the constraints imposed on the prosthesis will therefore be diminished.

In this context, it is beneficial to propose a prosthesis that allows a more efficiently fit to the profile of the spinal column and thus fully attain the goals it set by offering a surface of articulation.

SUMMARY

The purpose of the invention is to overcome some of the inconveniences of the prior art by proposing an intervertebral disc prosthesis at least comprising two plates each bearing at least an edge off-set in relation to the same edge of the other plate.

This goal is reached with an intervertebral disc prosthesis comprising at least two plates, namely first and second plates, articulated about each other by means of a curved surface, namely articulation, of at least one of the plates, allowing to pivot and/or tilt the plates in relation to each other, via rotation about, respectively, an axis substantially perpendicular to the plane of the plates and an axis substantially in the plane of the plates, each of the plates comprising a surface known as a contact surface, intended to be in contact with a vertebral plate of one of the vertebrae between which the prosthesis is intended to be implanted, this contact surface for each of the plates comprising a geometric centre at equal distance from at least two diametrically opposite points located on the periphery of the plate, characterised in that the geometric centres of the plates are not vertically aligned, this off-set of the geometrical centres of the plates engendering an off-set of the edges of the plates in at least one direction perpendicular to the vertical axis of the spinal column.

According to another feature, the second plate comprises a curved surface of articulation of which at least one part co-operates with a curved surface of articulation of the first plate for which it is complementary, in order to allow the articulation, by pivoting and/or tilting, of the plates in relation to each other, the prosthesis comprising a centre of articulation vertically aligned with the vertex of the curved surface of articulation of the second plate and corresponding to the mid-position of the centre of the curved surface of the first plate in relation to the second plate.

According to another feature, the curved surface of the first plate is concave and the curved surface of articulation of the second plate is convex.

According to another feature, the curved surface of the first plate is convex and the curved surface of articulation of the second plate is concave.

According to another feature, the prosthesis also comprises a core comprising a plane surface and a curved surface of articulation and in that only the first plate comprises a curved surface of articulation co-operating with at least one part of the curved surface of the core for which it is complementary, in order to allow the pivoting and/or tilting of the plates in relation to each other, the plane surface of the core co-operating with at least one part of a plane surface of the second plate in order to allow a translation and/or a rotation of the core in relation to the second plate in at least one direction perpendicular to the vertical axis of the spinal column, the second plate comprising means for co-operating complementary with means for co-operating of the core allowing to restrict or abolish at least this translation of the core in relation to the second plate, the prosthesis comprising a centre of articulation vertically aligned with the vertex of the curved surface of articulation of the core and corresponding to the mid-position of the core between the means for co-operating of the second plate and to the mid-position of the centre of the curved surface of the first plate in relation to the core.

According to another feature, the curved surface of the first plate is concave and the curved surface of the core is convex.

According to another feature, the curved surface of the first plate is convex and the curved surface of the core is concave.

According to another feature, the prostheses comprises a centre of articulation vertically aligned with the vertex of the curved surface of articulation, said centre of articulation being vertically aligned with the geometric centre of the first plate but off-set in relation to the geometric centre of the second plate in at least one direction perpendicular to the vertical axis of the spinal column, this off-setting of the geometric centres of the plates engendering an off-setting of the edges of the plates in at least one direction perpendicular to the vertical axis of the spinal column.

According to another feature, the prostheses comprises a centre of articulation vertically aligned with the vertex of the curved surface of articulation, said centre of articulation being off-set in relation to the geometric centre of the first plate but in the opposite direction to that of its off-setting in relation to the geometric centre of the second plate, so that the vertical projection of the centre of articulation is located between the vertical projections of the geometric centres of the plates and that the off-setting of the geometric centres in relation to the centre of articulation cumulate and engender an off-setting of the edges of the plates in at least one direction perpendicular to the vertical axis of the spinal column.

According to another feature, the prostheses comprises a centre of articulation vertically aligned with the vertex of the curved surface of articulation, said centre of articulation being off-set in relation to the geometric centre of the first plate, in the same direction as that of its off-setting in relation to the geometric centre of the second plate, but at a lesser distance so that these off-settings partially compensate each other and engender an off-setting of the edges of the plates between themselves in at least one direction perpendicular to the vertical axis of the spinal column.

According to another feature, the means for co-operating of the second plate are female means located in the vicinity of the edges of the second plate and co-operating with the male means of the core.

According to another feature, the dimensions of each male means for co-operating are slightly smaller than those of the female means for co-operating in order to allow a slight travel between the core and the second plate around the position corresponding to the vertical projection of the centre of articulation.

According to another feature, the dimensions of each male means for co-operating are substantially the same as those of each female means for co-operating in order to prevent any travel between the core and the second plate and to maintain the core in the position corresponding to the vertical projection of the centre of articulation.

According to another feature, the means for co-operating of the second plate are the male means located in the vicinity of the edges of the second plate and co-operating with the female means of the core.

According to another feature, the dimensions of each male means for co-operating are slightly smaller than those of each female means for co-operating in order to allow as slight travel between the core and the second plate, around the position corresponding to the vertical projection of the centre of articulation.

According to another feature, the dimensions of each male means for co-operating are substantially the same as those of each female means for co-operating in order to prevent any travel between the core and the second plate and to maintain the core in the position corresponding to the vertical projection of the centre of articulation.

According to another feature, the male means for co-operating of the core are two studs located on the two side edges of the core and the female means for co-operating of the second plate are four walls located, in pairs, on each of the two side edges of the second plate.

According to another feature, the female means for co-operating of the second plate comprise a section dish-shaped towards the centre of the plate and partly covering the male means for co-operating of the core in order to prevent the core from lifting.

According to another feature, the median planes representing the contact surfaces of the plates are substantially parallel or create an acute angle, the slope obtained by such an angle allowing to adapt the overall shape of the prosthesis to the anatomy of the spinal column or to possibly correct any slope defects of the vertebrae of the patient for whom the prosthesis is intended for.

According to another feature, the plates comprise, at least on their lower edge, at least a bevel facilitating the insertion of the prosthesis between the vertebrae.

According to another feature, the same plates can be assembled with cores of different thicknesses and/or dimensions and/or shapes.

According to another feature, the plates comprise mobile osseous anchorage means.

According to another feature, the osseous anchorage means and/or the plates comprise means for securing the binding of the osseous anchorage means on the plates.

According to another feature, the mobile osseous anchorage means of the plates consists in at least one plate equipped with notches oriented so as to prevent this notched plate from falling out once inserted in a vertebra, one end of the plate having an inward curving section and intended to be interlocked onto at least one edge of an opening located in the vicinity of the periphery of the plates.

According to another feature, the end of the notched plate, opposite the one with an inward curving section, comprises a bevel facilitating the insertion of the notched plate into the vertebrae.

According to another feature, the opening located in the vicinity of the periphery of the plates comprises a sloping section on which the notched plate leans when the curved section of the osseous anchorage means is interlocked onto the edge of this opening, this sloping section thus allowing to set the angle of the osseous anchorage means in relation to the plates and to guide them when being inserted into the opening.

According to another feature, the means for securing consist in flexible tabs oriented towards the curved section of the osseous anchorage means and intended to fold back against the edges of the plate when inserting the osseous anchorage means into the openings in the plates, then to spring back so as to lean against the limit stops located on the walls of the openings in the plates during the interlocking of the curved sections onto the edges of the openings in the plates, so as to prevent the osseous anchorage means from falling out.

According to another feature, the inward curving section of the notched plate of the mobile osseous anchorage means extends by means of a second plate also equipped with notches oriented so as to prevent the plate from falling out once inserted into the vertebra.

According to another feature, the mobile osseous anchorage means of the plates consist in at least a winglet equipped with notches oriented so as to prevent the winglet from falling out once inserted in a groove made in a vertebra, one end of the winglet having an inward curving section and intended to be interlocked on to at least one edge of an opening in the vicinity of the periphery of the plates.

According to another feature, the means for securing the winglet consist in at least one stud located on the lower surface of the winglet and intended to be interlocked into at least one hole in the contact surfaces of the plates, the stud and the hole being of complementary shape and size so as to secure the winglet in place on the plates.

BRIEF DESCRIPTION OF THE DRAWINGS

Other features and advantages of the invention will become clearer upon reading the following description, given in reference to the annexed figures, in which.

DETAILED DESCRIPTION OF THE EMBODIMENTS

Figure 1A:
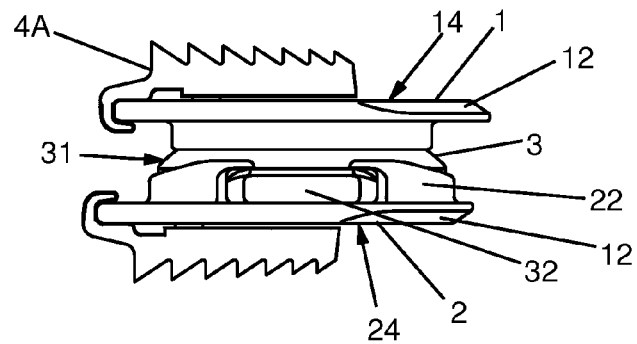
FIGS. 1A, 1B and 1C respectively represent a side view, a rear view with a cross section plane 1C-1C and a cross section along said plane 1C-1C, of an intervertebral disc prosthesis according to an embodiment of the invention, FIGS. 2A, 2B and 2C respectively represent a side view, a rear view with a cross section plane 2C-2C and a cross section along said plane 2C-2C, of an intervertebral disc prosthesis according to another embodiment of the invention, FIGS. 3A and 3B respectively represent a rear view with a cross section plane 3B-3B and a cross section along said plane 3B-3B, of an intervertebral disc prosthesis according to an embodiment of the invention and FIGS. 3C and 3D respectively represent a rear view with a cross section plane 3D-3D and a cross section along said plane 3D-3D, of an intervertebral disc prosthesis according to another embodiment of the invention, FIGS. 4A and 4B respectively represent a top view and a perspective view of an embodiment of the osseous anchorage means of an intervertebral disc prosthesis according to the invention, and FIGS. 4C and 4D respectively represent a top view and a side view of another embodiment of the osseous anchorage means of an intervertebral disc prosthesis according to the invention, FIGS. 5A, 5B and 5C respectively represent a perspective view, a top view and a side view of an intervertebral disc prosthesis according to different embodiments of the invention.

The invention relates to an intervertebral disc prosthesis comprising at least two plates (1, 2) off-set in relation to each other so as to more efficiently follow the anatomy of the spinal column. As explained in the preamble of this application, the vertebrae are generally slightly off-set to each other, so that their edges, for example posterior, are not vertically aligned. The prosthesis according to the invention is thus designed so that the edges of the plates (1, 2) are not vertically aligned and have a slight off-setting corresponding to an off-setting between the edges of the vertebrae between which the prosthesis is intended to be inserted. The off-setting of the vertebrae could have been accurately measured beforehand, in order to choose a prosthesis whose off-setting of the plates (1, 2) perfectly corresponds to the off-setting of the vertebrae.

The plates (1 and 2) of the prosthesis according to the invention each comprise a geometric centre (G1 and G2, respectively) which can be defined, generally speaking, by a point at equal distance from two diametrically opposite points located on the periphery of the plates (1, 2). Normally, the plates of the intervertebral disc prostheses have a relatively straightforward shape and their geometric centre can be of equal distance from all the points located on the periphery of the plates. Irrespective of the prosthesis, a geometric centre can be defined by a point or a surface located at equal distance from the edges of the plate. The geometric centres (G1, G2) of the plates (1, 2) of the prosthesis according to the invention are not vertically aligned but are off-set to each other in at least one direction, for example antero-posterior, perpendicular to the vertical axis of the spinal column The two plates (1 and 2) of a single intervertebral disc prosthesis are usually substantially the same size and this off-set (D) of the geometric centres (G1, G2) of the plates engenders an off-set of the edges of the plates (1, 2). In the case of a prosthesis whose plates are not of the same size, it is envisaged to off-set the edges of the plates (1 and 2) and the geometric centres (G1, G2) will be even more off-set to each other.

In the different embodiments described below, the prosthesis comprises at least two plates (1 and 2), namely first (1) and second (2) plates, articulated about each other by means of a curved surface (11, 31), namely articulation, of at least one of the plates. This curved surface (11, 31) of articulation allows to pivot the plates (1, 2) about each other, via rotation about an axis substantially perpendicular to the plane of the plates and/or to tilt the plates (1, 2) about each other, via rotation about an axis substantially along the plane of the plates (1, 2). Each of the plates (1, 2) comprises a surface (14, 24) known as a contact surface, intended to be in contact with a vertebral plate of one of the vertebrae between which the prosthesis is intended to be inserted. The geometric centre will hereafter be defined in relation to this contact surface for the sake of ease but it must be understood that it is the vertical axis passing through the geometric centre which matters in the principle of the invention and that the exact position of the geometric centre on the width of the plates has no relevance. In the different embodiments described below, each of the plates (1, 2) therefore comprises a geometric centre (G1, G2) at equal distance from at least two diametrically opposite points located on the periphery of the plate (1, 2). The geometric centres (G1, G2) of the plates (1, 2) are not vertically aligned and this off-set (D) of the geometrical centres (G1, G2) of the plates engenders an off-set of the edges of the plates (1, 2) in at least one direction perpendicular to the vertical axis of the spinal column.

Figure 2A:
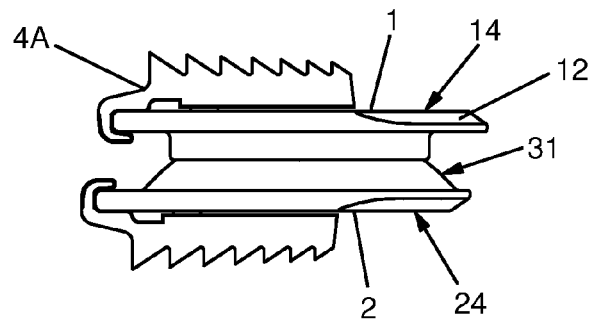
Figure 2B:
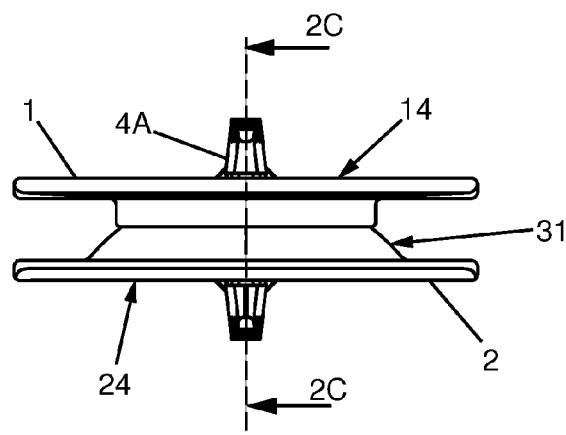
Figure 2C:
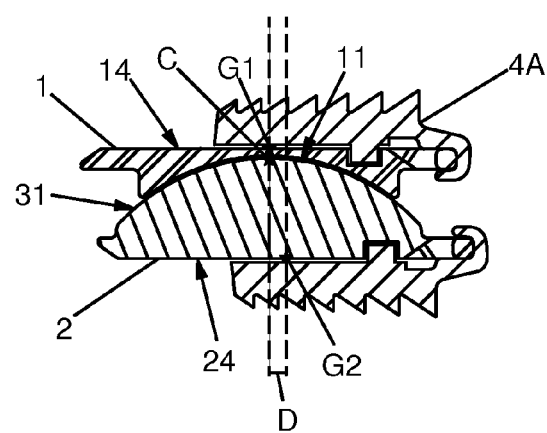
Figure 3A:
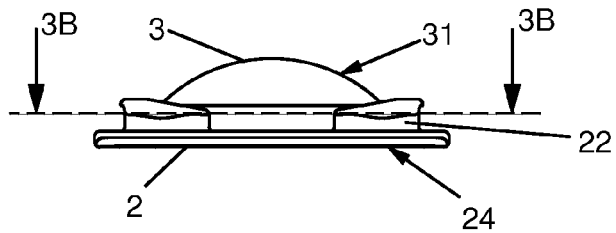
Figure 3B:
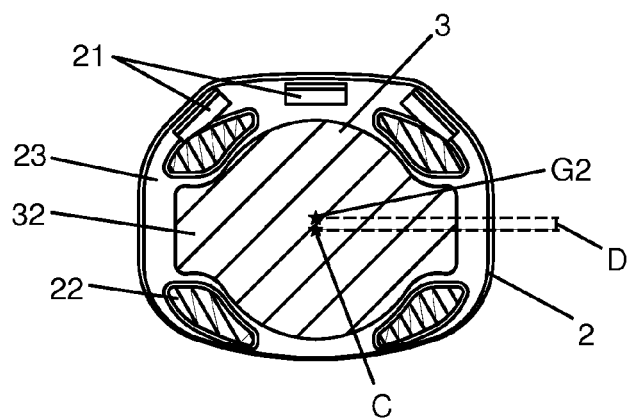
Figure 3C:
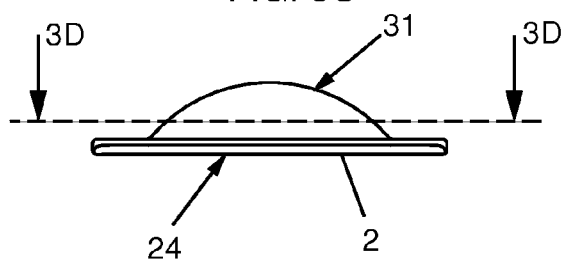
Figure 3D:
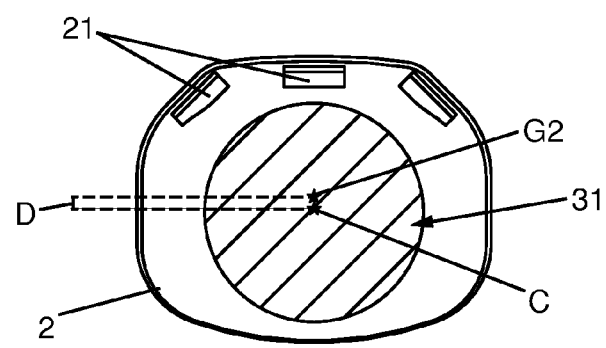
Figure 4A:
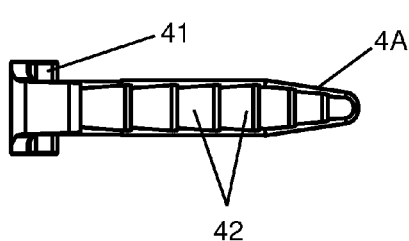
Figure 4B:
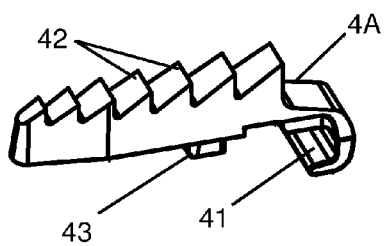
Figure 4C:
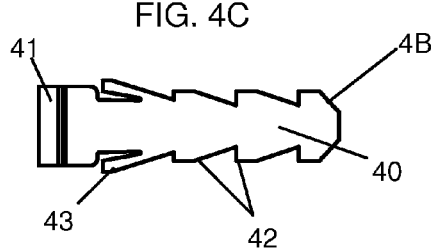
Figure 4D:
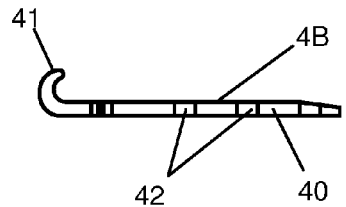

In the embodiment represented in FIGS. 2A, 2B, 2C, 3C and 3D, the prosthesis only comprises two elements: two plates (1, 2). In this case, the second plate (2) comprises a curved surface (31) of articulation of which at least one section co-operates with a curved surface (11) of articulation of the first plate (1) to which it is complementary. The co-operating of these curved surfaces (11, 31) of articulation allows to pivot and/or tilt the plates (1, 2) about each other. A centre (C) of articulation vertically aligned with the vertex of the curved surface (31) of articulation of the second plate (2) can be defined. This centre (C) of articulation corresponds to the mid-position of the centre of the curved surface (11) of the first plate (1) compared to the second plate (2). In the embodiment represented in the figures, the curved surface (11) of the first plate (1) is concave and the curved surface (31) of articulation of the second plate (2) is convex but it can be the case that the curved surface (11) of the first plate (1) is convex and that the curved surface (31) of articulation of the second plate (2) is concave.

Figure 1B:
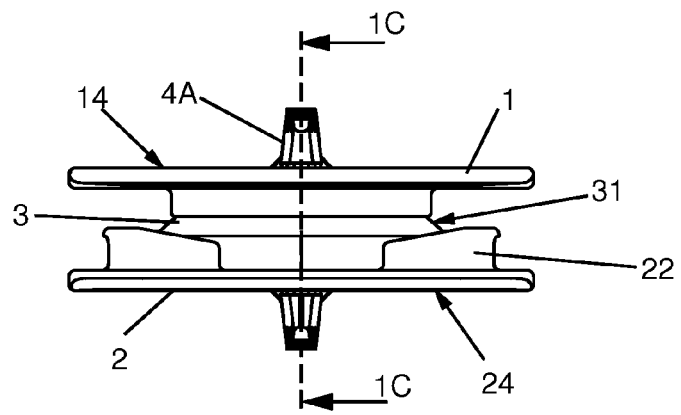
Figure 1C:
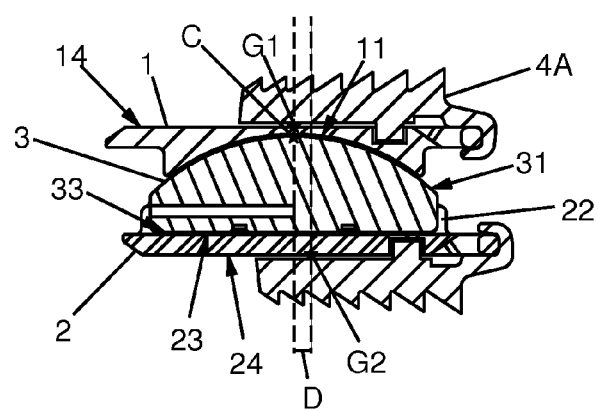
Figure 5A:
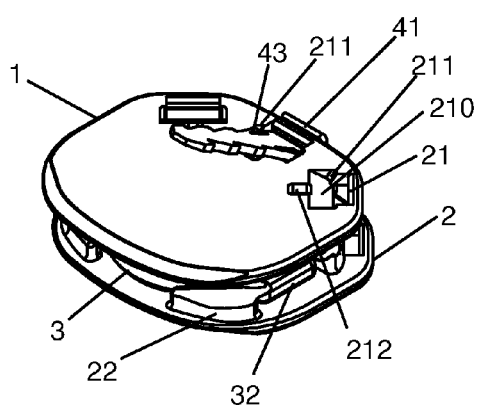
Figure 5B:
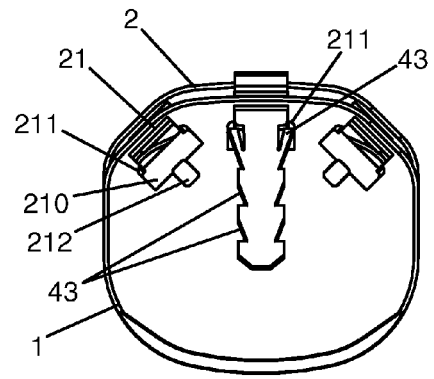
Figure 5C:
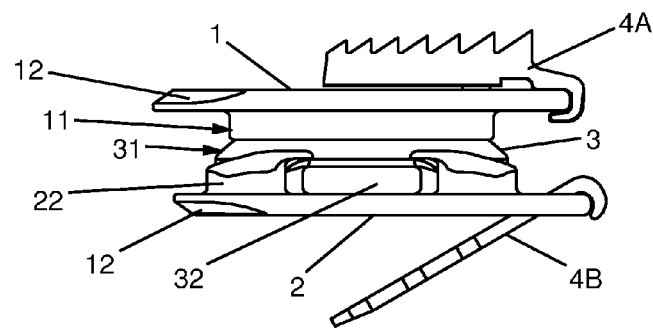

In the embodiment represented in FIGS. 1A to 1C, 3A, 3B and 5A to 5C, the prosthesis also comprises a core (3) comprising a plane surface (33) and a curved surface (31) of articulation. In the case of a prosthesis with three elements, only the first plate (1) comprises a curved surface of articulation (11) and this surface co-operates with at least a section of the curved surface (31) of the core (3) to which it is complementary, to allow to pivot and/or tilt the plates (1, 2) about each other. The plane surface (33) of the core (3) co-operates with at least a section of a plane surface (23) of the second plate (2) to allow a translation of the core (3) in relation to the second plate (2) in at least one direction perpendicular to the vertical axis of the spinal column and/or a rotation of the core (3) in relation to the second plate (2) via rotation about an axis substantially perpendicular to the plane of these plane surfaces. The second plate (2) comprises means for co-operating (22) which are complementary with means for co-operating (32) of the core (3) so as to restrict or abolish at least this translation of the core (3) in relation to the second plate (2). In the embodiments represented in figures, the means for co-operating (22) of the second plate (2) are female means located in the vicinity of the edges of the second plate (2) and co-operating with the male means (32) of the core (3). In the embodiments represented in the figures, these male means for co-operating (32) of the core (3) are two studs located on the two side edges of the core (3) and the female means for co-operating (22) of the second plate (2) are four walls located, in pairs, on each of the two side edges of the second plate (2). These walls comprise an inward curving section towards the centre of the plate (2) and partially covering the male means for co-operating (32) of the core (3) so as to prevent the core (3) from lifting. In another embodiment of the invention, the means for co-operating (22) of the second plate (2) can be male means located in the vicinity of the edges of the second plate (2) and co-operating with the female means (32) of the core (3). In an embodiment of the invention, the dimensions of each male means for co-operating (32, 22) can be slightly smaller than those of the female means for co-operating (22, 32) so as to allow a slight travel between the core (3) and the second plate (2) around the position corresponding to the vertical projection of the centre (C) of articulation. In another embodiment, the dimensions of each male means for co-operating (32, 22) can be substantially identical to those of each female means for co-operating (22, 32) so as to prevent any travel between the core (3) and the second plate (2) and to retain the core (3) in the position corresponding to the vertical projection of the centre (C) of articulation.

In this case of a prosthesis with three elements, the centre (C) of articulation is vertically aligned with the vertex of the curved surface (31) of articulation of the core (3) and correspond to the mid-position of the core (3) between the means for co-operating (22) of the second plate (2) and to the mid-position of the centre of the curved surface (11) of the first plate (1) in relation to the core (3). In the embodiment represented in the figures, the curved surface (11) of the first plate (1) is concave and the curved surface (31) of the core (3) is convex but it could be that the curved surface (11) of the first plate (1) is convex and that the curved surface (31) of the core (3) is concave.

In an embodiment of the invention, the centre (C) of articulation is vertically aligned with the centre (G1) of geometry of the first plate (1) but off-set in relation to the geometric centre (G2) of the second plate (2) in at least a direction perpendicular to the vertical axis of the spinal column. This off-setting (D) of the geometric centres (G1, G2) of the plates engenders an off-setting of the edges of the plates (1, 2) in at least one direction perpendicular to the vertical axis of the spinal column. In another embodiment of the invention, the centre (C) of articulation can also be off-set in relation to the geometric centre (G1) of the first plate (1). This off-setting of the centre (C) of articulation in relation to the geometric centre (G1) of the first plate (1) can be in the opposite direction to that of its off-setting (D) in relation to the geometric centre (G2) of the second plate (2) so that the vertical projection of the centre (C) of articulation lies between the vertical projections of the geometric centres (G1, G2) of the plates (1, 2) and so that the off-setting of the geometric centres (G1, G2) in relation to the centre (C) of articulation cumulate and engender an off-setting of the edges of the plates (1, 2) in at least one direction perpendicular to the vertical axis of the spinal column. This off-setting of the centre (C) of articulation in relation to the geometric centre (G1) of the first plate (1) can also be in the same direction as that of its off-setting (D) in relation to the geometric centre (G2) of the second plate (2), but at a lesser distance so that these off-settings partially compensate each other and engender an off-setting of the edges of the plates (1, 2) between themselves in at least one direction perpendicular to the vertical axis of the spinal column.

It can be beneficial that prostheses according to various embodiments of the invention allow correction of the slope defects of the adjacent vertebrae. The median planes representing the contact surfaces (14, 24) of the plates (1, 2) can therefore be substantially parallel or create an acute angle. The slope obtained by such an angle will allow the overall shape of the prosthesis to be adapted to the anatomy of the spinal column or to correct any possible slope defects of the vertebrae of the patient for whom the prosthesis is intended. The same plates (1, 2) are assembled with core (3) of different thicknesses and/or dimensions and/or shapes. The plates (1, 2) can comprise, at least on their anterior edge, at least a bevel (12) facilitating the insertion of the prosthesis between the vertebrae.

An embodiment of a prosthesis according to the invention comprises mobile osseous anchorage means (4A, 4B) allowing to anchor the plates (1, 2) in the vertebrae. These osseous anchorage means (4A, 4B) and/or the plates (1, 2) can thus comprise means for securing (43 and/or 211, 212) of the binding of the osseous anchorage means (4A, 4B) on the plates (1, 2).

In one embodiment of the mobile osseous anchorage means (4B), at least a plate (40), equipped with notches (42) oriented so as to prevent this notched plate (40) from falling out once inserted in a vertebra, is intended to be interlocked on to at least one edge (21) of an opening in the vicinity of the periphery of the plates (1, 2), thanks to an inwardly curved section (41). Thus, these mobile osseous anchorage means (4B) can be inserted into the vertebrae and interlocked on to the plates of the prosthesis once the latter has been inserted between the vertebrae. This embodiment of the mobile osseous anchorage means (4B) allows a possible adjustment of the position of the prosthesis between the vertebrae prior to definitive bonding. The end of the notched plate (40) opposite the one with an inwardly curved section (41) can comprise a bevel allowing to facilitate the insertion of the notched plate (40) into the vertebrae. The opening in the vicinity of the periphery of the plates (1, 2) can comprise a sloping section (210) on to which the notched plate (40) leans when the curved section (41) of the osseous anchorage means (4B) is interlocked on to the edge (21) of this opening This sloping section (210) allows to set the angle of the osseous anchorage means (4B) in relation to the plates and to guide them when they are being inserted into the opening. The means for securing (43) can consist of flexible tabs (43) oriented towards the curved section (41) of the osseous anchorage means (4B) and intended to fold back against the edges of the plate (40) when inserting the osseous anchorage means (4B) into the openings in the plates (1, 2). During the interlocking of the curved sections (41) onto the edges (21) of the openings in the plates (1, 2), these flexible tabs (43) separate to lean against the limit stops (211) located on the walls of the openings in the plates (1, 2), so as to prevent the osseous anchorage means (4B) from falling out. In an alternative embodiment, the inwardly curved section (41) of the notched plate (40) of the mobile osseous anchorage means (4B) extends via a second plate also equipped with notches (42) oriented so as to prevent the plate from falling out once inserted into the vertebrae.

In another embodiment the mobile osseous anchorage means (4A, 4B) of the plates (1, 2) includes at least one winglet (4A) equipped with notches (42) oriented so as to prevent the winglet (4A) from falling out once inserted into a groove made in a vertebra. One end of the winglet (4A) has an inwardly curved section (41) intended to be interlocked on to at least one edge (21) of an opening in the vicinity of the periphery of the plates (1, 2). The means for securing (43) of the winglet (4A) can thus comprise at least a stud (43) located on the lower surface of the winglet (4A) and intended to be interlocked into at least one hole (210) on the contact surfaces (14, 24) of the plates (1, 2). The stud (43) and the hole (210) will be of complementary shape and size so as to secure the winglet (4A) on to the plates (1, 2). In this embodiment, the vertebrae, between which the prosthesis is intended to be inserted, will have been previously prepared by the surgeon by hollowing out, in the vertebral plates, grooves of complementary shape and size with the shape and size of the winglets (4A).

It should be obvious for those skilled in the art that the invention allows embodiments under numerous other specific forms whilst remaining within the scope of the invention as claimed. Consequently, the embodiments should be considered as purely illustrative, but can be modified in the field defined by the impact of the attached claims, and the invention should not be restricted to the aforementioned details.

The invention claimed is:

1. An intervertebral device comprising:
    a first side having a plate-like surface configured for contacting a first vertebra;
    a second side having a plate-like surface configured for contacting a second vertebra;
    a first end configured to facilitate insertion of the device into the space between the first and second vertebrae;
    a second end located on the opposite side of the device from the first end; and
    a first generally rectangular opening extending angularly through at least one of the plate-like surfaces along the second end and comprising
        a top wall, a bottom wall, and a pair of lateral side walls spaced apart to house a first plate-like anchor with the top surface of the first plate-like anchor adjacent to the top wall, the bottom surface of the first plate-like anchor adjacent to the bottom wall, and lateral side surfaces of the first plate-like anchor adjacent to respect ones of the lateral side walls,
        a sloping section configured to receive the first plate-like anchor, to guide the first plate-like anchor during insertion of the first plate-like anchor into a vertebra, and to set the angle of the first plate-like anchor with respect to one of the first and second sides of the device, and
        a limit stop disposed on at least one of the lateral side walls configured to engage a locking tab disposed on a lateral side surface of the first plate-like anchor and lock the anchor against the device.

2. The intervertebral device of claim 1 in which the first end is beveled.

3. The intervertebral device of claim 1 comprising plural limit stops.

4. The intervertebral device of claim 1 further comprising a second angled opening along the second end having a sloping section configured to receive a second plate-like anchor for the device, to guide the second plate-like anchor during insertion of the second plate-like anchor into a vertebra, and to set the angle of the second plate-like anchor with respect to one of the first and second sides of the device.

5. The intervertebral device of claim 4 in which the first and second angled openings open on the first side of the device.

6. The intervertebral device of claim 4 in which the first angled opening opens on the first side of the device and the second angled opening opens on the second side of the device.

7. The intervertebral device of claim 1 in which each of the first and second sides comprises at least one angled opening.

8. A combination comprising:
    a first elongated anchor having
        a first end configured to facilitate insertion of the first elongated anchor into a vertebra,
        a plate-like body having a rectangular transverse cross section and comprising top and bottom surfaces having a width and a pair of lateral side surfaces having a height, with the width greater than the height, and notches along at least one of the lateral side surfaces configured to facilitate retention of the first elongated anchor in the vertebra,
        a retainer for an intervertebral device located at a second end, and
        a resilient locking tab extending from one of the lateral side surfaces of the plate-like body at a point between the first end and the second end, proximal to the second end; and
    an intervertebral device having
        a first side having a surface configured for contacting a first vertebra;
        a second side having a surface configured for contacting a second vertebra;
        a first end having a bevel configured to facilitate insertion of the device into the space between the first and second vertebrae;
        a second end located on the opposite side of the device from the first end; and
        a first angled opening along the second end having a sloping section comprising four internal walls configured to receive the first elongated anchor, to guide the first elongated anchor during insertion of the first elongated anchor into a vertebra, and to set the angle of the first elongated anchor with respect to one of the first and second sides of the device, the angled opening having plural internal limit stops disposed on opposing internal walls and configured to engage a resilient locking tab disposed on an first elongated anchor and lock the first elongated anchor against the device.

9. The combination of claim 8 in which the first end of the first elongated anchor is beveled.

10. The anchor of claim 9 in which the curved portion comprises the retainer.

11. The combination of claim 9 in which the locking tab has an insertion position in which the locking tab is compressed and a locking position in which the locking tab is relaxed.

12. The combination of claim 8 in which the first elongated anchor comprises a curved portion.

13. The combination of claim 8 in which the retainer comprises an interlock.

14. The combination of claim 8 in which the device further comprises a second angled opening along the second end having a sloping section configured to receive a second elongated anchor for the device, to guide the second elongated anchor during insertion of the second elongated anchor into a vertebra, and to set the angle of the second elongated anchor with respect to one of the first and second sides of the device.

15. The combination of claim 14 in which the first and second angled openings open on the first side of the device.

16. The combination of claim 14 in which the first angled opening opens on the first side of the device and the second angled opening opens on the second side of the device.

17. The combination of claim 8 in which each of the first and second sides comprises at least one angled opening.

18. A method for implantation of an intervertebral device comprising:
   providing a combination in accordance with claim 8;
   inserting the intervertebral device between adjacent vertebrae;
   inserting the first elongated anchor through the first angled opening;
   using the first angled opening to guide the first elongated anchor into one of the vertebrae; and
   using the first angled opening to set the angle of the first elongated anchor with respect to the one of the vertebrae in which the first elongated anchor is inserted.

19. The method of claim 18 further comprising abuting the retainer on a stop of the device so as to fix the device to the vertebra.

20. The method of claim 18 further comprising adjusting the position of the intervertebral device after it is inserted between the adjacent vertebrae.

21. The method of claim 18 in which the first elongated anchor has a curved portion.

22. The method of claim 18 in which the combination further is in accordance with claim 14 and further comprising:
   inserting the second elongated anchor through the second angled opening;
   using the second angled opening to guide the second elongated anchor into one of the vertebrae; and
   using the second angled opening to set the angle of the second elongated anchor with respect to the one of the vertebrae in which the second elongated anchor is inserted.

23. The method of claim 22 further comprising abuting the retainer on a stop of the device so as to fix the device to the vertebra.

24. The method of claim 22 in which the first elongated anchor has a curved portion and the second elongated anchor has a curved portion.

* * * * *